(12) United States Patent
Parunak

(10) Patent No.: US 6,575,188 B2
(45) Date of Patent: Jun. 10, 2003

(54) METHODS AND SYSTEMS FOR FLUID CONTROL IN MICROFLUIDIC DEVICES

(75) Inventor: Gene Parunak, Ann Arbor, MI (US)

(73) Assignee: Handylab, Inc., Ann Arbor, MI (US)

( * ) Notice: Subject to any disclaimer, the term of this patent is extended or adjusted under 35 U.S.C. 154(b) by 0 days.

(21) Appl. No.: 09/953,921

(22) Filed: Sep. 18, 2001

(65) Prior Publication Data

US 2003/0019522 A1 Jan. 30, 2003

Related U.S. Application Data

(60) Provisional application No. 60/307,638, filed on Jul. 26, 2001.

(51) Int. Cl.[7] .............................................. F16K 13/10
(52) U.S. Cl. ........................ 137/251.1; 137/827; 251/11
(58) Field of Search ............................. 137/828, 251.1, 137/252; 251/11

(56) References Cited

U.S. PATENT DOCUMENTS

| | | | |
|---|---|---|---|
| 1,616,419 A | * 2/1927 | Wilson ...................... 137/251.1 |
| 1,773,401 A | * 8/1930 | Lovekin ....................... 137/74 |
| 3,528,449 A | * 9/1970 | Witte et al. ............... 137/251.1 |
| 4,139,005 A | * 2/1979 | Dickey ......................... 137/74 |
| 4,612,959 A | * 9/1986 | Costello ................... 137/251.1 |
| 4,654,127 A | 3/1987 | Baker et al. ................. 204/1 T |
| 4,673,657 A | 6/1987 | Christian .................... 436/501 |
| 4,946,562 A | 8/1990 | Guruswamy ............. 204/153.1 |
| 4,949,742 A | * 8/1990 | Rando et al. ................ 137/828 |
| 4,963,498 A | 10/1990 | Hillman et al. ............... 436/69 |
| 4,989,626 A | * 2/1991 | Takagi et al. ................ 137/828 |
| 5,001,417 A | 3/1991 | Pumphrey et al. .......... 324/71.5 |
| 5,004,583 A | 4/1991 | Guruswamy et al. .......... 422/58 |
| 5,053,199 A | 10/1991 | Keiser et al. .............. 422/68.1 |
| 5,061,336 A | 10/1991 | Soane ......................... 156/245 |
| 5,064,618 A | 11/1991 | Baker et al. ............. 422/82.01 |
| 5,071,531 A | 12/1991 | Soane ...................... 204/182.8 |
| 5,126,002 A | 6/1992 | Iwata et al. .................. 156/468 |
| 5,126,022 A | 6/1992 | Soane et al. .............. 204/180.1 |
| 5,135,627 A | 8/1992 | Soane ...................... 204/182.8 |
| 5,135,872 A | 8/1992 | Pouletty et al. ............. 436/180 |
| 5,147,606 A | 9/1992 | Charlton et al. .............. 422/56 |
| 5,208,163 A | 5/1993 | Charlton et al. .............. 436/63 |
| 5,250,263 A | 10/1993 | Manz .......................... 422/81 |
| 5,282,950 A | 2/1994 | Dietze et al. ................ 204/406 |
| 5,296,375 A | 3/1994 | Kricka et al. ............... 435/291 |
| 5,304,477 A | 4/1994 | Nagoh et al. ................ 435/134 |
| 5,304,487 A | 4/1994 | Wilding et al. ............. 435/291 |

(List continued on next page.)

OTHER PUBLICATIONS

Handique and Burns, 2001, "Mathematical Modelling of Drop Mixing in a Silt–Type Microchannel", J. Micromech. Microeng. 11:548–554.

Handique et al., 2001, "On–Chip Thermopneumatic Pressure for Discrete Drop Pumping," Anal. Chem. 73:1831–1838.

Handique et al., 2000, "Nanoliter Liquid Metering in Microchannels Using Hydrophobic Patterns," Anal. Chem. 72:4100–4109.

Burns et al., 1998, "An Integrated Nanoliter DNA Analysis Device," Science 282:484–487.

Primary Examiner—John Rivell
(74) Attorney, Agent, or Firm—Pennie & Edmonds LLP

(57) ABSTRACT

The present invention relates to a valve for use in a microfluidic system. The valve includes a substrate defining an upstream channel and a downstream channel joined by a passage, wherein the passage comprises a first opposed wall disposed at an angle to a central axis of the upstream channel. A thermally responsive substance (TRS) obstructs the passage. At least a portion of the TRS that obstructs the passage abuts the first opposed wall. Upon the actuation of the heat source in thermal contact with the TRS an opening motion of the TRS opens the passage.

34 Claims, 16 Drawing Sheets

U.S. PATENT DOCUMENTS

| | | | | |
|---|---|---|---|---|
| 5,316,727 | A | 5/1994 | Suzuki et al. | 422/68.1 |
| 5,339,486 | A | 8/1994 | Persic, Jr. | 15/244.1 |
| 5,372,946 | A | 12/1994 | Cusak et al. | 436/69 |
| 5,374,395 | A | 12/1994 | Robinson et al. | 422/64 |
| 5,411,708 | A | 5/1995 | Moscetta et al. | 422/81 |
| 5,427,946 | A | 6/1995 | Kricka et al. | 435/291 |
| 5,486,335 | A | 1/1996 | Wilding et al. | 422/55 |
| 5,498,392 | A | 3/1996 | Wilding et al. | 422/68.1 |
| 5,503,803 | A | 4/1996 | Brown | 422/102 |
| 5,519,635 | A | 5/1996 | Miyake et al. | 364/497 |
| 5,559,432 | A | 9/1996 | Logue | 324/207.17 |
| 5,565,171 | A | 10/1996 | Dovichi et al. | 422/68.1 |
| 5,569,364 | A | 10/1996 | Hooper et al. | 204/455 |
| 5,580,523 | A | 12/1996 | Bard | 422/50 |
| 5,585,069 | A | 12/1996 | Zanucchi et al. | 422/100 |
| 5,585,089 | A | 12/1996 | Queen et al. | 424/133.1 |
| 5,587,128 | A | 12/1996 | Wilding et al. | 422/50 |
| 5,589,136 | A | 12/1996 | Northrup et al. | 422/102 |
| 5,593,838 | A | 1/1997 | Zanzucchi et al. | 435/6 |
| 5,599,432 | A | 2/1997 | Manz et al. | 204/451 |
| 5,599,503 | A | 2/1997 | Manz et al. | 422/82.05 |
| 5,603,351 | A | 2/1997 | Cherukuri et al. | 137/597 |
| 5,605,662 | A | 2/1997 | Heller et al. | 422/68.1 |
| 5,628,890 | A | 5/1997 | Carter et al. | 204/403 |
| 5,631,337 | A | 5/1997 | Sassi et al. | 526/307.2 |
| 5,632,876 | A | 5/1997 | Zanzucchi et al. | 204/600 |
| 5,632,957 | A | 5/1997 | Heller et al. | 422/68.1 |
| 5,635,358 | A | 6/1997 | Wilding et al. | 435/7.2 |
| 5,637,469 | A | 6/1997 | Wilding et al. | 435/7.21 |
| 5,639,423 | A | 6/1997 | Northrup et al. | 122/50 |
| 5,643,738 | A | 7/1997 | Zanzucchi et al. | 435/6 |
| 5,646,039 | A | 7/1997 | Northrup et al. | 435/287.2 |
| 5,652,149 | A | 7/1997 | Mileaf et al. | 436/518 |
| 5,674,742 | A | 10/1997 | Northrup et al. | 435/286.5 |
| 5,681,484 | A | 10/1997 | Zanzucchi et al. | 216/2 |
| 5,681,529 | A | 10/1997 | Taguchi et al. | 422/61 |
| 5,683,657 | A | 11/1997 | Mian | 422/68.1 |
| 5,699,157 | A | 12/1997 | Parce | 356/344 |
| 5,726,026 | A | 3/1998 | Wilding et al. | 435/7.21 |
| 5,731,212 | A | 3/1998 | Gavin et al. | 436/526 |
| 5,747,666 | A | 5/1998 | Willis | 73/1.02 |
| 5,750,015 | A | 5/1998 | Soane et al. | 204/454 |
| 5,755,942 | A | 5/1998 | Zanzucchi et al. | 204/454 |
| 5,763,262 | A | 6/1998 | Wong et al. | 435/287.2 |
| 5,770,029 | A | 6/1998 | Nelson et al. | 204/604 |
| 5,772,966 | A | 6/1998 | Maracas et al. | 422/100 |
| 5,779,868 | A | 7/1998 | Parce et al. | 204/604 |
| 5,787,032 | A | 7/1998 | Heller et al. | 365/151 |
| 5,788,814 | A | 8/1998 | Sun et al. | 204/297 |
| 5,800,690 | A | 9/1998 | Chow et al. | 204/451 |
| 5,827,481 | A | 10/1998 | Bente et al. | 422/81 |
| 5,842,106 | A | 11/1998 | Thaler et al. | 419/8 |
| 5,842,787 | A | 12/1998 | Kopf-Sill et al. | 366/340 |
| 5,846,396 | A | 12/1998 | Zanzucchi et al. | 204/601 |
| 5,849,486 | A | 12/1998 | Heller et al. | 435/6 |
| 5,849,489 | A | 12/1998 | Heller | 435/6 |
| 5,849,598 | A | 12/1998 | Wilson et al. | 436/180 |
| 5,852,495 | A | 12/1998 | Parce | 356/344 |
| 5,856,174 | A | 1/1999 | Lipshutz et al. | 435/286.5 |
| 5,858,188 | A | 1/1999 | Soane et al. | 204/454 |
| 5,863,502 | A | 1/1999 | Southgate et al. | 422/58 |
| 5,863,708 | A | 1/1999 | Zanzucchi et al. | 430/320 |
| 5,863,801 | A | 1/1999 | Southgate et al. | 436/63 |
| 5,866,345 | A | 2/1999 | Wilding et al. | 435/7.21 |
| 5,869,004 | A | 2/1999 | Parce et al. | 422/100 |
| 5,872,010 | A | 2/1999 | Karger et al. | 436/173 |
| 5,874,046 | A | 2/1999 | Megerle | 422/68.1 |
| 5,876,675 | A | 3/1999 | Kennedy | 422/99 |
| 5,880,071 | A | 3/1999 | Parce et al. | 204/453 |
| 5,882,465 | A | 3/1999 | McReynolds | 156/285 |
| 5,883,211 | A | 3/1999 | Sassi et al. | 526/307.2 |
| 5,885,432 | A | 3/1999 | Hooper et al. | 204/469 |
| 5,885,470 | A | 3/1999 | Parce et al. | 216/33 |
| 5,895,762 | A | 4/1999 | Greenfield et al. | 436/43 |
| 5,900,130 | A | 5/1999 | Benvegnu et al. | 204/453 |
| 5,912,124 | A | 6/1999 | Kumar | 435/6 |
| 5,912,134 | A | 6/1999 | Shartle | 435/7.24 |
| 5,916,522 | A | 6/1999 | Boyd et al. | 422/58 |
| 5,916,776 | A | 6/1999 | Kumar | 435/91.1 |
| 5,919,711 | A | 7/1999 | Boyd et al. | 436/178 |
| 5,922,591 | A | 7/1999 | Anderson et al. | 435/287.2 |
| 5,927,547 | A | 7/1999 | Papen et al. | 222/57 |
| 5,928,880 | A | 7/1999 | Wilding et al. | 435/7.21 |
| 5,929,208 | A | 7/1999 | Heller et al. | 530/333 |
| 5,932,799 | A | 8/1999 | Moles | 75/53.01 |
| 5,935,401 | A | 8/1999 | Amigo | 204/454 |
| 5,939,291 | A | 8/1999 | Loewy et al. | 435/91.2 |
| 5,942,443 | A | 8/1999 | Parce et al. | 436/514 |
| 5,948,227 | A | 9/1999 | Dubrow | 204/455 |
| 5,955,028 | A | 9/1999 | Chow | 422/63 |
| 5,955,029 | A | 9/1999 | Wilding et al. | 422/68.1 |
| 5,957,579 | A | 9/1999 | Kopf-Sill et al. | 366/340 |
| 5,958,203 | A | 9/1999 | Parce et al. | 204/451 |
| 5,958,694 | A | 9/1999 | Nikiforov | 435/6 |
| 5,959,291 | A | 9/1999 | Jensen | 250/214 |
| 5,964,995 | A | 10/1999 | Nikiforov et al. | 204/450 |
| 5,964,997 | A | 10/1999 | McBride | 204/451 |
| 5,965,001 | A | 10/1999 | Chow et al. | 204/600 |
| 5,965,410 | A | 10/1999 | Chow et al. | 435/91.2 |
| 5,965,886 | A | 10/1999 | Sauer et al. | 250/332 |
| 5,972,187 | A | 10/1999 | Parce et al. | 204/453 |
| 5,976,336 | A | 11/1999 | Dubrow et al. | 204/453 |
| 5,980,704 | A | 11/1999 | Cherukuri et al. | 204/269 |
| 5,980,719 | A | 11/1999 | Cherukuri et al. | 204/600 |
| 5,989,402 | A | 11/1999 | Chow et al. | 204/601 |
| 5,992,820 | A | 11/1999 | Fare et al. | 251/129.01 |
| 5,993,611 | A | 11/1999 | Moroney, III et al. | 204/157.6 |
| 5,993,750 | A | 11/1999 | Ghosh et al. | 422/191 |
| 5,997,708 | A | 12/1999 | Craig | 204/601 |
| 6,001,231 | A | 12/1999 | Kopf-Sill | 204/454 |
| 6,001,307 | A | 12/1999 | Naka et al. | 422/81 |
| 6,004,515 | A | 12/1999 | Parce et al. | 422/100 |
| 6,007,690 | A | 12/1999 | Nelson et al. | 204/601 |
| 6,012,902 | A | 1/2000 | Parce | 417/48 |
| 6,043,080 | A | 3/2000 | Lipshutz et al. | 435/287.2 |
| 6,046,056 | A | 4/2000 | Parce et al. | 436/514 |
| 6,048,734 | A | 4/2000 | Burns et al. | 436/180 |
| 6,054,034 | A | 4/2000 | Soane et al. | 204/601 |
| 6,056,860 | A | 5/2000 | Amigo et al. | 204/454 |
| 6,057,149 | A | 5/2000 | Burns et al. | 435/287.2 |
| 6,130,098 | A | 10/2000 | Handique et al. | 436/180 |
| 6,168,948 | B1 | 1/2001 | Anderson et al. | 435/287.2 |
| 6,287,254 | B1 | 9/2001 | Dodds | 600/300 |
| 6,306,273 | B1 | 10/2001 | Wainright et al. | 204/454 |

* cited by examiner

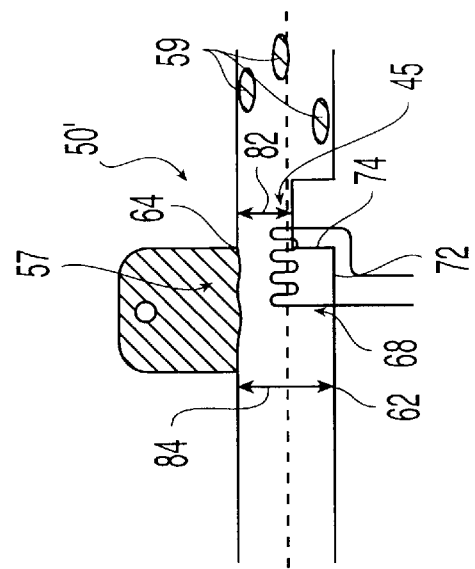
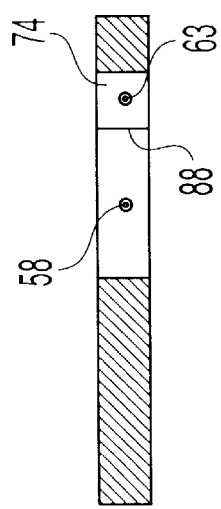
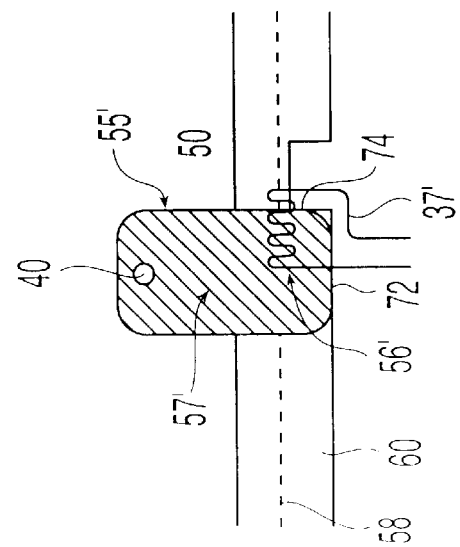

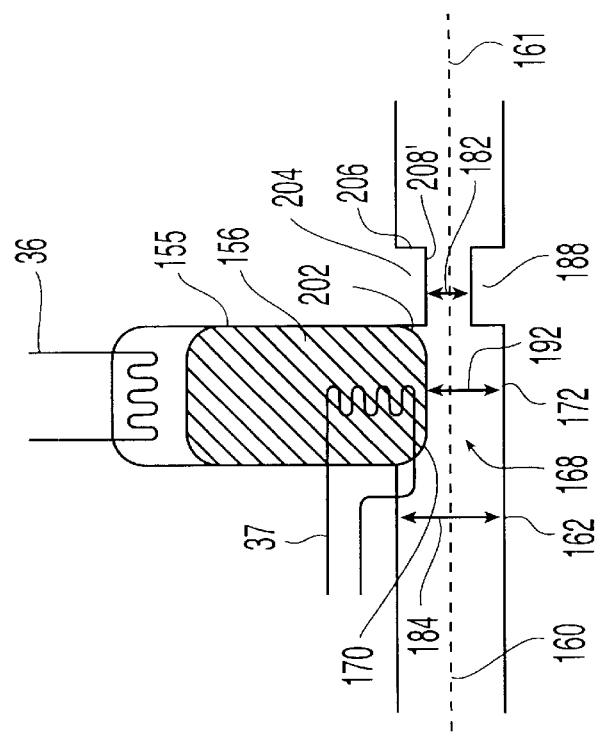
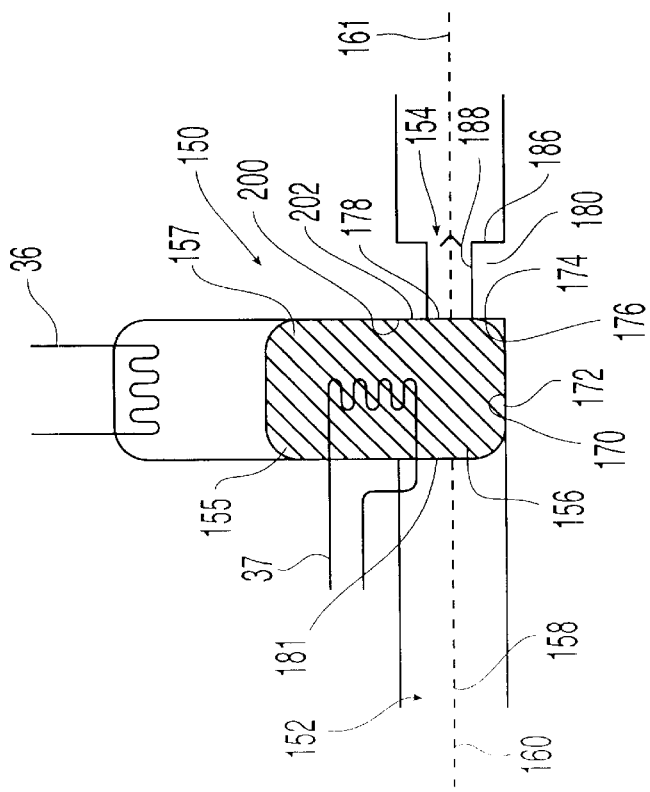

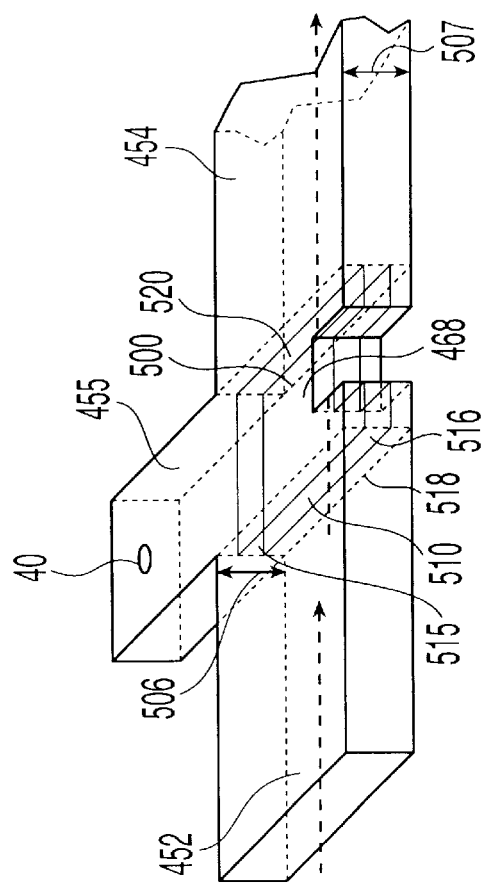
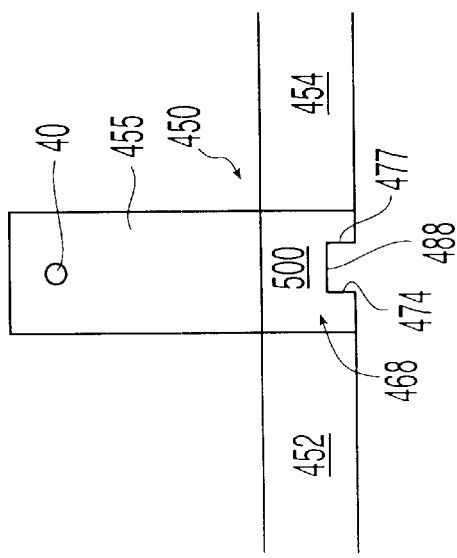
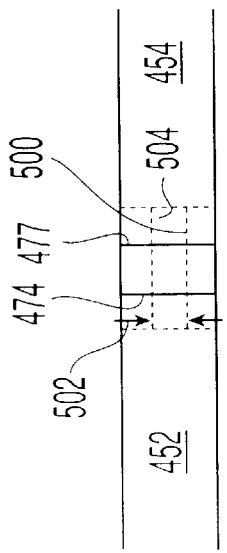
Fig. 11a
Fig. 11b
Fig. 11c

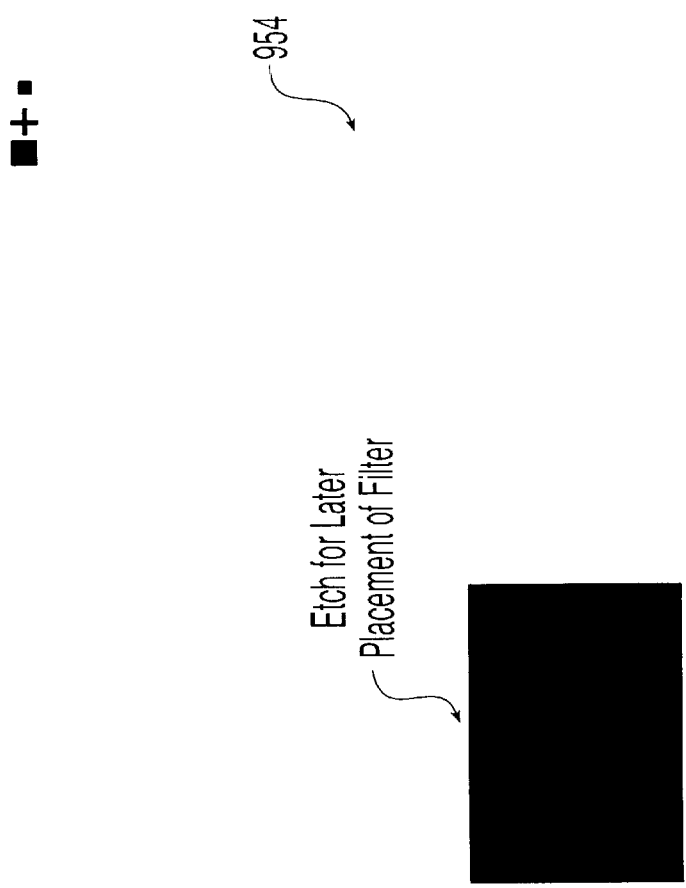

METHODS AND SYSTEMS FOR FLUID
CONTROL IN MICROFLUIDIC DEVICES

RELATED APPLICATIONS

This application claims priority to provisional application No. 60/307,638 filed Jul. 26, 2001, which application is incorporated herein in its entirety.

FIELD OF THE INVENTION

The present invention relates to methods and components for manipulating samples using microfluidic systems. More particularly, the invention relates to microfluidic systems for concentrating particles, such as bacterial cells, entrained in a fluid.

BACKGROUND

Microfluidic systems include devices with features having dimensions on the order of nanometers to 100s of $\mu$m that cooperate to perform various desired functions. In particular, micro fluidic devices perform material analysis and manipulation functions, such as to perform chemical or physical analyses.

One type of micro fluidic technology allows the manipulation of discrete amounts of materials, such as samples and reagents, in addition to continuous, flowing streams of material. Such devices are disclosed in, for example, U.S. Pat. Nos. 6,057,149, issued May 2, 2000 and titled "Microscale Devices And Reactions In Microscale Devices;" 6,048,734, issued Apr. 11, 2000 and titled "Thermal Microvalves in a Fluid Flow Method;" and 6,130,098, issued Oct. 10, 2000. In these devices, motive forces, such as gas pressure, are used as to urge material from one region of the device to another. For example, a sample can be pushed or drawn to a processing chamber where it is reacted with a reagent similarly moved into the chamber. Because each device can have many other chambers or channels that intersect with the processing chamber, valves can be used to isolate material in one region of the device from other regions of the device. An ideal valve would prevent leakage when closed and remain closed even when excess pressure acts upon the closed valve.

Citation or identification of any reference in this Section or any section of this application shall not be construed that such reference is available as prior art to the present invention.

SUMMARY OF THE INVENTION

The present invention relates to a valve for use in a microfluidic system, comprising a substrate defining an upstream channel and a downstream channel joined by a passage, the passage comprising a first surface, and a thermally responsive substance (TRS) disposed, when the valve is in the closed state, to substantially obstruct the passage, wherein pressure present in the upstream channel urges at least a portion of the TRS against the first surface. Preferably, the passage defines a central axis and the first surface is disposed at an angle to the central axis. Upon opening the passage, at least a portion of TRS may melt and enter the downstream channel.

In one embodiment the valve further comprises a heat source in thermal contact with the TRS, wherein, upon actuation of the heat source, an opening motion of the TRS opens the passage.

The passage may further comprises a second surface disposed at a second angle to the central axis. At least a second portion of the TRS that obstructs the passage abuts the second surface. The first and second surfaces may protrude into the passage. The first and second surfaces form a restriction therebetween.

Another embodiment of the invention relates to a method for producing a valve for a microfluidic system, comprising providing a substrate defining a passage that joins an upstream and a downstream channel of the microfluidic system, the passage comprising a retaining surface and introducing a mass of temperature responsive material (TRS) into the passage, wherein, when the valve is in the closed state, pressure in the upstream channel urges the TRS against the retaining surface.

Yet another embodiment of the invention relates to a method for producing a valve for a microfluidic system, comprising providing a substrate defining a passage that joins an upstream and a downstream channel of the microfluidic system; and introducing a mass of temperature responsive material (TRS) into a reservoir channel adjacent the passage, wherein capillary action draws the TRS into the passage, and wherein a surface tension of the TRS substantially prevents the TRS in the passage from entering the upstream or downstream channel.

One embodiment of the invention relates to a valve for providing a passage between an upstream and a downstream channel of a microfluidic system, the valve comprising a temperature responsive substance (TRS), wherein, at a first temperature, the TRS is disposed to obstruct the passage, and wherein, at a second temperature, at least a portion of the (TRS) enters the downstream channel, thereby opening the passage.

At least about 75% of the TRS that obstructs the passage may enter the downstream channel upon the opening of the passage.

Another embodiment of the invention relates to a valve for providing a passage between upstream and downstream channels of a microfluidic system, comprising a temperature responsive substance (TRS) configured to substantially obstruct the passage and a heat source disposed in thermal contact with the (TRS), wherein, upon actuation of the heat source, at least a portion of the (TRS) enters the downstream channel, thereby opening the passage. Pressure present in the upstream channel preferably urges at least a portion of the TRS against the first surface.

Another embodiment of the invention relates to a microfluidic system, comprising a substrate defining a processing chamber, a source channel, and a downstream channel, the source channel joining the processing chamber at a first point and the downstream channel joining the processing chamber at a second point a thermally responsive substance (TRS) disposed to obstruct a passage between the processing chamber and downstream channel; and a heat source in thermal contact with the TRS, wherein, upon actuation of the heat source, at least a portion of the TRS enters the downstream channel, thereby opening the passage.

Another aspect of the invention relates to a valve for use in a microfluidic system, comprising a substrate defining an upstream channel and a downstream channel joined by a passage and a thermally responsive substance (TRS) disposed to substantially obstruct the passage, wherein a length of the TRS obstructing the passage is greater than a width of the upstream channel adjacent the passage. A heat source is in thermal contact with the TRS, wherein, upon actuation of the heat source, an opening motion of the TRS opens the passage.

Another embodiment of the invention relates to a valve for use in a microfluidic system, comprising a substrate defining a first and second channel joined by a passage, the first channel and the passage defining an opening therebetween, a thermally responsive substance (TRS) disposed to substantially obstruct the passage, wherein a height of opening is less than a height of the first channel adjacent the opening such that capillary action draws TRS into the passage and a surface tension of the TRS substantially prevents the TRS from entering the first or second channel, and a heat source in thermal contact with the TRS, wherein, upon actuation of the heat source, an opening motion of the TRS opens the passage.

BRIEF DESCRIPTION OF THE DRAWINGS

The present invention is described below in reference to the following drawings, in which:

FIG. 2b shows an open state of the valve of FIG. 1a;

FIG. 3a shows a perspective cross sectional view of the valve of claim 1a;

FIG. 3b shows a cross sectional view taken along section 3b of FIG. 3a;

FIG. 4a shows a closed state of another valve of the invention;

FIG. 4b shows an open state of the valve of FIG. 3a;

FIG. 5a shows a closed state of another valve of the invention;

FIG. 5b shows an open state of the valve of FIG. 4a;

FIG. 6b shows an open state of the valve of FIG. 5a;

FIG. 7b shows an open state of the valve of FIG. 6a;

FIG. 8b shows an open state of the valve of FIG. 7a;

FIG. 9b shows an open state of the valve of FIG. 8a;

FIG. 10b shows an open state of the valve of FIG. 9a;

FIG. 11a shows a top view of another valve of the invention;

FIG. 11b shows a side view of the valve of FIG. 10a;

FIGS. 11c and 11d show a perspective, cut-away view of the valve of FIG. 10a;

FIGS. 13a–13d show photolithigraphic masks suitable for fabricating a system according to the invention;

DETAILED DESCRIPTION OF THE INVENTION

Figure 1:
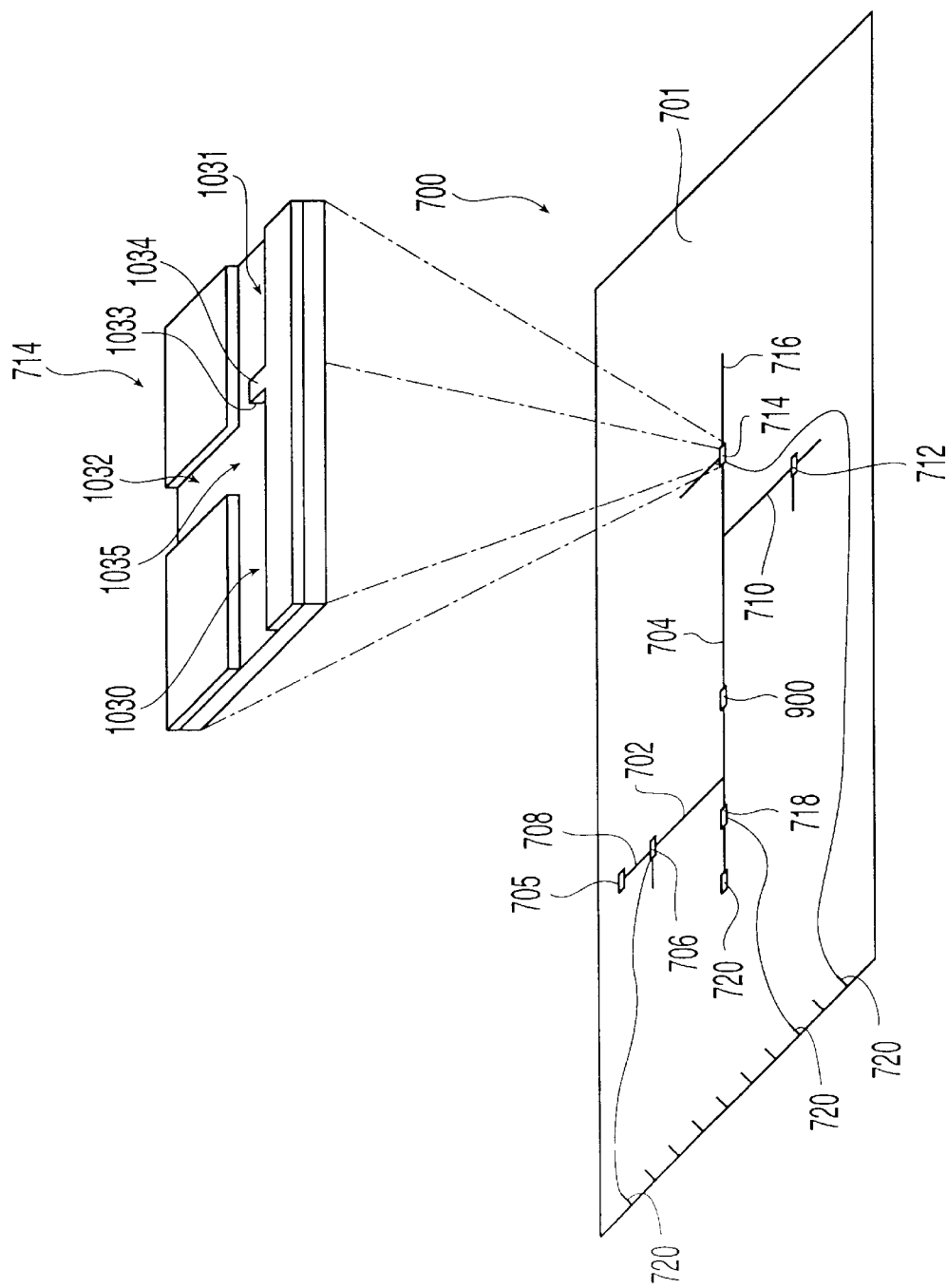
FIG. 1 shows a microfluidic system according to the invention.

The present invention relates to improved valves for microfluidic systems and microfluidic systems comprising the improved valves. Referring to FIG. 1, a microfluidic system 700 of the invention is configured to perform analyses using minute amounts of material, such as samples and reagents, which can be transported among different regions of the system. The different regions include, for example, chambers, channels and passages, as discussed below. An important feature of microfluidic system 700 is the capability of regulating the passage of material between its different regions. For example, system 700 includes a valve 706, which regulates the passage of material between a material introduction channel 702 and a chamber 704. When valve 706 is open, material can be introduced into chamber 704 for processing, such as by concentrating, diluting, mixing, or reacting the material. Once a desired amount of material has been introduced, valve 706 can be closed to substantially prevent additional material from entering along channel 702. Valve 706 operates as a multi-use valve, which can be toggled between the opened and closed states without loss of performance.

Figure 2B:
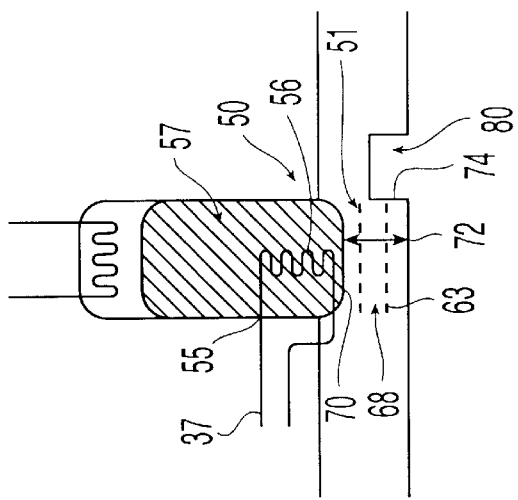
Figure 2A:
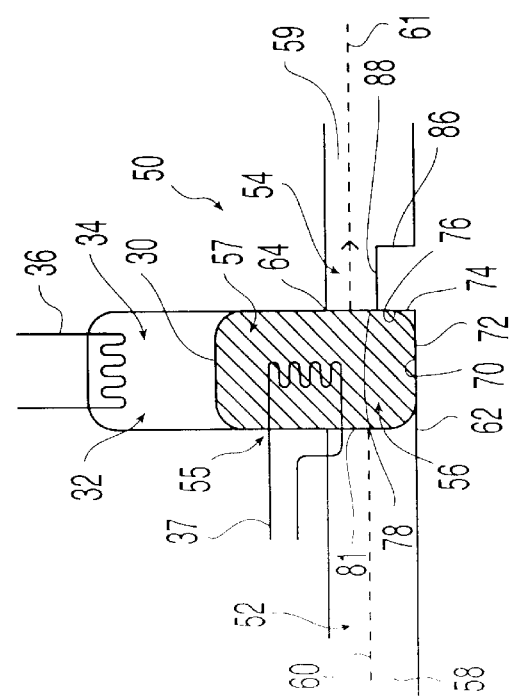
FIG. 2a shows a closed state of a valve of the invention.

An embodiment of such a multi-use valve 50 is shown in FIGS. 2a and 2b. Valve 50 regulates the passage of material between a first channel 52 and a second channel 54. A valve passage 68 connects the channels through the valve. In the open state, FIG. 2b, TRS 56 is retracted into a valve reservoir 55 to allow the passage of material from one channel to the other. In the closed state, FIG. 2a, a mass of temperature responsive material (TRS) 56 substantially obstructs passage 68. The closed valve substantially prevents the passage of material between channels 52, 54.

The valve opening operation preferably includes actuating a heat source 37 to heat TRS 56 thereby modifying a physical or chemical property thereof, such as by making TRS 56 softer. A cooler 36 cools a gas 34 trapped in contact with an end 30 of TRS 56. The resulting contraction of gas 32 decreases the pressure acting upon end 30 and retracts the softened TRS 56 into reservoir 55. To close valve 50, gas 32 is heated, which expands the gas thereby increasing the pressure acting upon end 30 and extending TRS 56 across passage 68.

Preferred embodiments of valves of the present invention include one or more elements configured to prevent leakage of a valve even when excess pressure acts upon the TRS obstructing the valve passage. Excess pressure occurs when the pressure present at one side of the valve is greater than the pressure present at the other side. For example, excess upstream pressure means that the pressure acting upon the upstream side of the valve from the upstream channel is greater than the pressure acting upon the downstream side of the valve from the downstream channel. Preferably, the at least one element is a surface that is disposed in opposition to a material transport path, which is the path taken by material passing through the open valve. When the valve is closed the excess upstream pressure urges the TRS against the opposed surface rather than causing leakage through the obstructed passage.

Returning to FIG. 2a, the TRS that obstructs passage 68, extends from a reservoir 55 to a valve wall 72. Reservoir 55 includes an amount of TRS 57 that is offset from passage 68 so that TRS 57 does not obstruct the passage of material through the valve. Reservoir 55 is preferably disposed on an opposite side of a passage central axis 63 from valve wall 72. At least a first abutting portion 70 of TRS 56 abuts wall 72. As used herein, the term "abuts" means that any remaining space between an abutting portion of a TRS and a wall of a closed valve is sufficiently small to substantially prevent the passage of material, such as a liquid, therethrough. Preferably, the portion of a TRS that abuts a wall, touches the wall, essentially eliminating the space therebetween.

Wall 72 includes a first opposed wall portion 74, which is preferably disposed at an angle to passage central axis 51. A second abutting portion 76 of TRS 56 abuts first opposed wall portion 74 when valve 50 is closed. Second abutting portion 76 and first opposed wall portion 74 substantially prevent passage of material through valve 50 even when the pressure acting upon an upstream portion 81 of TRS 56 exceeds the pressure applied to a downstream portion 78 of TRS 56. Excess upstream pressure urges second abutting portion 76 against opposed wall surface 74, thereby closing valve 50 more securely. In the absence of an opposed wall portion, excess upstream pressure can distort the configuration of a TRS obstructing a valve passage, which could permit the undesirable leakage of material through the valve.

Figure 3A:
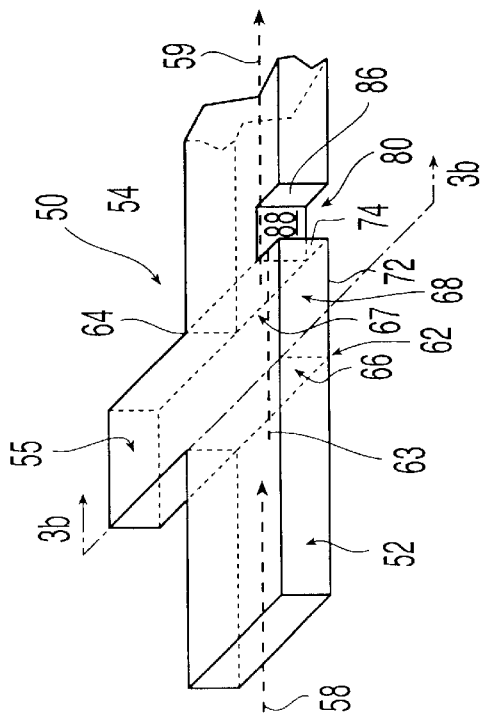

First opposed wall portion 74 is preferably integral with a wall projection 80 that extends into a path taken by material passing through passage 68. Thus, at least some material entering passage 68 via an upstream cross sectional area 66 must pass around projection 80. For example, FIGS. 3a and 3b show that a material transport path 63 from an upstream point 62 into passage 68 is obstructed by opposed wall portion 74. In general, a material transport path is the path taken by material, such as a sample and or reagent, in proceeding from an upstream location toward a downstream location. With respect to a particular valve, the terms upstream and downstream refer to the preferred direction of material transport through the valve. It should be understood, however, that a valve can be operated to permit or obstruct the passage of material from a downstream side of the valve to an upstream side.

Projection 80 includes a second opposed wall surface 86 and an outer wall 88. A wall 90 of second channel 54 is disposed on the opposite side of central axis 61 from outer wall 88. Because projection 80 extends beyond wall 72, a distance 82 between outer wall 88 and wall 90 is smaller than a corresponding distance 84 between opposed walls of first channel 52 at upstream point 62. Downstream distance 82 is at least 10% smaller, preferably at least 20% smaller, and more preferably at least 30% smaller than upstream distance 84. Thus, projection 80 and wall 90 define a restriction, where a cross sectional area 67 of a downstream material transport path 59 is less than cross sectional area 66 of an upstream material transport path 58. The smaller downstream cross sectional area adjacent the valve increases the capacity of valve 50 to withstand greater upstream pressure without excessive leakage. The presence of projection 80 also offsets a central axis 61 of second channel 54 from a central axis 60 of first channel 52. Although projection 80 is shown as generally rectangular, alternative projections having other shapes such as triangular or shapes with arcuate surfaces can be used.

Valve 50 operates to open or close passage 68 upon a change of the temperature of TRS 56 from a first to a second, preferably higher temperature. Actuation of a heat source 37, which is in thermal contact with at least a portion of TRS 56 and 57, provides sufficient thermal energy to change a physical or chemical characteristic of the heated portion of TRS. Preferably, the change in characteristic is a softening or a decrease in size that is sufficient to allow a motion of at least TRS 56 with respect to passage 68. Valve 50 can be repeatedly switched between the opened and closed states without a significant loss of material 56 or capacity to prevent passage of material through the valve when closed.

A temperature responsive material (TRS) refers to a material that exhibits a change in at least one physical or chemical characteristic upon a transition from a first temperature to a second, different temperature. The mass of TRS that obstructs a valve passage can be an essentially solid mass or an agglomeration of smaller particles that cooperate to obstruct the passage. Examples of TRS's include, but are not limited to, solder, wax, polymers, plastics, and combinations thereof. Preferably, the characteristic is at least one of a decreased hardness and a decreased size. For example, in one embodiment, the TRS melts upon a transition from a first temperature to a second, higher temperature. The TRS that melts is a meltable substance that may be, for example, a wax (for example, an olefin) or a eutectic alloy (for example, a solder). The first and second temperatures are preferably insufficiently high to damage materials, such as nearby electronic components or the device substrate. The second temperature is preferably from 40° to 90° C. and most preferably from 50° to 70° C.

In a preferred embodiment, the TRS, does not disperse upon melting but merely softens. In an alternative embodiment, the TRS is a substance having a coefficient of thermal expansion that is different from the material forming the obstructed passage. Heating or cooling the passage and TRS causes the TRS to expand or contract relative to the passage. In the contracted state, the TRS can be actuated to move in or out of the channel, as described below.

The term passage refers to the region within a valve that is obstructed by a mass of TRS with the valve fully closed. When the valve is fully open, the passage is the region through which material, such as a liquid, can pass through the valve from an upstream location to a downstream location. Thus, surfaces of the valve reservoir are not part of the passage because material in the passage is preferably excluded from passing into the reservoir. The "mass of TRS" refers to an amount of TRS sufficient to substantially obstruct the valve passage, thereby substantially preventing the passage of material through the valve. Substantially preventing the passage of material prevents the passage of an amount of material that would undesirably deplete the volume of a micro-droplet located upstream from the valve. Similarly, substantially preventing the passage of material prevents upstream material from adversely impacting micro-droplets located downstream from the valve. For example, the concentration of or pH of the downstream droplet remains essentially unchanged when upstream material is blocked by a closed valve. Preferably, a closed valve completely prevents the passage of any liquid or particle adjacent the valve.

Referring to FIG. 2b, an open state of valve 50 is shown in which TRS 56 has been essentially fully retracted into reservoir 55 to open passage 68, thereby permitting passage of material through valve 50 from at least one of the first and second channels to the other. By essentially fully retracted, it is meant that essentially all of TRS 56, which had obstructed passage 68, is retracted into reservoir 55 rather than remaining in passage 68 or dispersing downstream of valve 50. Upon fully retracting TRS 56, not more than about 10%, preferably not more than about 5%, and most preferably not more than about 2% of TRS 56 is left behind in passage 68 and dispersed downstream of valve 50.

The opening motion is preferably driven by decreasing the pressure upon end 30 of TRS 57 relative to the pressure acting upon TRS abutting portion 70. The decreased pressure preferably occurs upon the contraction of a fluid, such as gas 32 present in actuating portion 34 of reservoir 55. The contraction of gas 32 can be obtained by cooling the gas to decrease the gas temperature and volume. Gas 32 is preferably cooled by actuating a cooler, such as a Peltier cooler in thermal contact with gas 32. The cooler is preferably integral with the substrate comprising valve 50 and with heat source 36. It should be understood, however, that the cooler can be located in a separate device that receives the substrate during operation.

The preferred open state of valve 50 permits passage of material being transported from first channel 52 to second channel 54. An opening distance 92 from abutting TRS portion 70 to wall 72 is sufficiently large to allow material to be passed through passage at a desired material transport rate. In the fully open state, opening distance 92 is preferably at least as great as distance 82 of second channel 54. It should be understood, however, that valve 50 can be operated in a partially open state, in which opening distance 92 is less than distance 82.

Valve 50 operates to close passage 68 when a closing motion of TRS 56 moves TRS abutting portion 70 across passage 68 to abut wall 72. The closing motion is preferably driven by pressure acting upon end 30. The pressure is obtained by the expansion of a fluid, such as gas 32. The expansion of gas 32 is preferably obtained by increasing the temperature of the gas by actuating a heat source 36 in thermal contact with gas 32. Heat source 36 is preferably integral with the substrate comprising valve 50. It should be understood, however, that the heat source can be located in an auxiliary device that accommodates the substrate during operation.

Referring to FIGS. 4a and 4b, a valve 50' having a different opening operation is shown. The opening of valve 50' is actuated by changing the temperature of at least a portion of a mass of TRS 56', which obstructs passage 68. Actuation of a heat source 37', which is in thermal contact with TRS 56' provides the thermal energy to raise TRS 56' from a first temperature to a second, preferably higher temperature. The second temperature is preferably sufficient to allow TRS 56' to melt or disperse, thereby opening passage 68. The portion of TRS 56' that is raised to the second temperature is sufficient to open passage 68.

Rather than retracting into a reservoir 55', at least about 30%, preferably at least about 75%, and more preferably at least about 90% of TRS 56' enters second channel 54, downstream from valve 50'. Thus, a valve of type 50' is a gate-type valve as distinguished from valve 50 in which material retracts into a reservoir to open the valve. The entry of TRS 56' into the downstream channel is preferably assisted by the application of excess upstream pressure against TRS 56'. The upstream pressure can be provided using a source of gas pressure in fluid communication with the upstream channel.

Although at least a portion of TRS 56' enters the downstream channel upon opening passage 68, gate type valves, such as valve 50', of the invention can be returned to the closed state once opened. For example, additional TRS can be made to flow from the reservoir associated with the gate valve into the passage by heating at least the associated reservoir.

Heat source 37' is preferably configured to heat a downstream length 45 of second channel 54' to a temperature sufficient to prevent dispersing or melting TRS from obstructing second channel 54'. Length 45' is at least 50% and preferably at least 75% as long as a length of passage 68 obstructed by TRS 56'. Heat source 37' heats the walls of the adjacent portion of the downstream channel to a temperature sufficient to at least often and preferably melt or disperse TRS 56. Thus, as seen in FIG. 4a, a portion of dispersed or melted TRS 56' can be deposited within downstream channels in small volumes TRS 59' that have a size insufficient to obstruct a downstream channel. TRS 56' can also be formed of a material that opens passage 68' without melting. For example, in one alternative embodiment, the obstructing TRS is formed of an agglomeration of particles. Upon a transition to a higher temperature, the agglomerated particles disperse downstream thereby opening the valve.

Valve 50' includes a reservoir 55', which allows TRS 56' and 57' to be introduced into passage 68' and reservoir 55', respectively. To load TRS in passage 68', the passage and reservoir are heated, such as by an external heat source, and TRS is introduced into an access port 40'. Once the TRS has just obstructed the passage, the external heat source is removed. TRS 56' then obstructs passage 68' of valve 50', which operates similarly to valve 50 by preventing leakage in response to upstream pressure.

Upon actuating heat source 37', the temperature of TRS 57' in reservoir 55' is preferably not raised by an amount sufficient to disperse or melt TRS 57'. Thus, substantially all of TRS 57' remains essentially stationary in reservoir 55' so that access port 40 is not brought into fluid communication with passage 68'. The lower temperature of TRS 57' can be maintained by limiting the duration of heat applied to TRS 56' and by increasing the distance of access port 40 from passage 68.

Referring to FIG. 5a, a valve 150 having two downstream abutting portions is shown in a closed state. When valve 150 is closed, a mass of temperature responsive material 156 obstructs material transport through a passage 168 between first and second channels 152, 154. A first abutting portion 170 of TRS 156 abuts a wall 172 of closed valve 150. Wall 172 includes a first opposed wall portion 174, which is disposed at an angle to central axis 160 and material transport path 158. Thermally responsive substance 156 includes a second abutting portion 176 disposed to abut first opposed wall portion 174 when valve 150 is closed. A third abutting portion 200 of TRS 156 abuts an opposed wall portion 202 of valve 150. Opposed wall portion 202 is disposed on an opposite side of central axis 161 from opposed wall portion 174, preferably adjacent a reservoir of TRS 155.

Abutting portions 176, 200 and wall surfaces 174, 202 are configured and disposed to prevent undesirable leakage through valve 150 when the pressure acting upon an upstream portion 181 of TRS 156 exceeds the pressure acting upon a downstream portion 178. The excess upstream pressure preferably urges abutting portions 176 and 200 against opposed wall portions 174 and 202, respectively, thereby closing valve 150 more securely. The presence of two downstream opposed walls decreases the tendency of TRS 56 to distort in response to upstream pressure.

First opposed wall surface 174 is preferably integral with a first wall projection 180 that extends into a material transport path 156 of first channel 52. Projection 180 includes a second opposed wall portion 186 and an outer wall surface 188. Opposed wall portion 202 is integral with a second wall projection 204 that also extends into material transport path 156. Projection 204 includes a second opposed wall portion 206 and an outer wall portion 208.

A distance 182 between outer wall portions 188, and 90 is preferably smaller than a corresponding distance 184 between opposed walls of first channel 152 at a point 162 upstream from valve 150. Distance 182 is at least 10% smaller, preferably at least 20% smaller, and more preferably at least 30% smaller than upstream distance 184. Thus, opposed wall portions 174, 202 or projections 180, 204 define a restriction therebetween. The restriction has a smaller cross sectional area than a cross sectional area at upstream point 162. Although projections 180 and 204 are shown as generally rectangular, projections having other shapes such as triangular or shapes with arcuate surfaces can be used.

Referring to FIG. 5b, an open state of valve 150 is shown in which TRS 156 has been essentially fully retracted into reservoir 155 to open passage 168, thereby permitting passage of material through valve 150 from at least one of the first and second channels to the other. In the fully open state, an opening distance 192 from abutting TRS portion 170 to wall 172 is preferably at least as great distance 182 of second channel 54. It should be understood, however, that valve 50 can be operated in a partially open state, in which opening distance 192 is less than distance 182. As discussed for valve 50 above, an open state of valve 150 can be repositioned repeatedly between the opened and closed states without a significant loss of material 156 or capacity to prevent transport of material when closed.

Figure 6B:
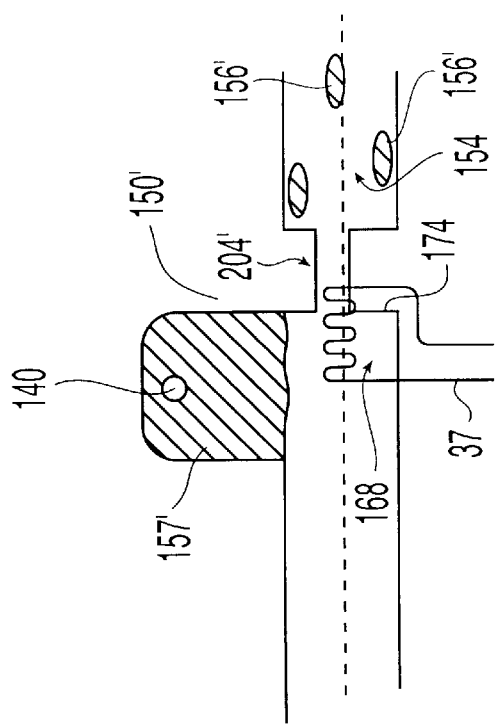
Figure 6A:
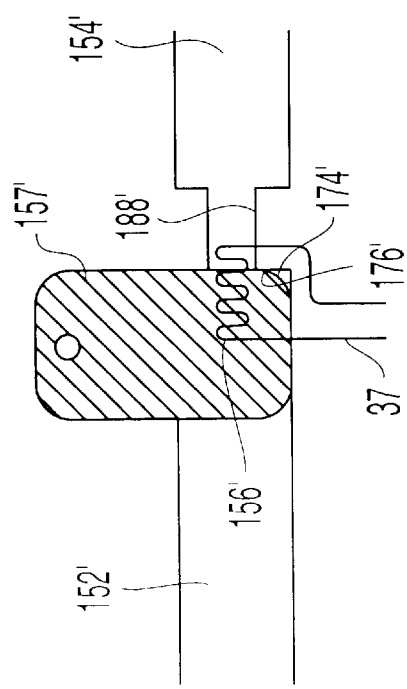
FIG. 6a shows a closed state of another valve of the invention.

A valve 150', seen in FIGS. 6a and 6b operates similarly to valve 150 in the closed state. In opening passage 68, valve 150' operates similarly to valve 50' in that a mass of TRS 156' obstructing passage 68 disperses or melts, thereby opening passage 68. The dispersal or melting preferably occurs upon actuation of a heat source 37 in thermal contact with TRS 156'.

Figure 7B:
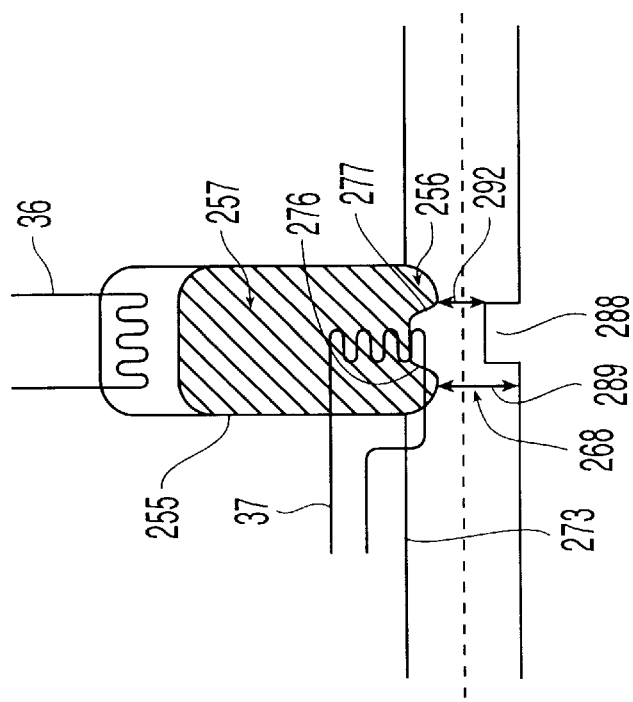
Figure 7A:
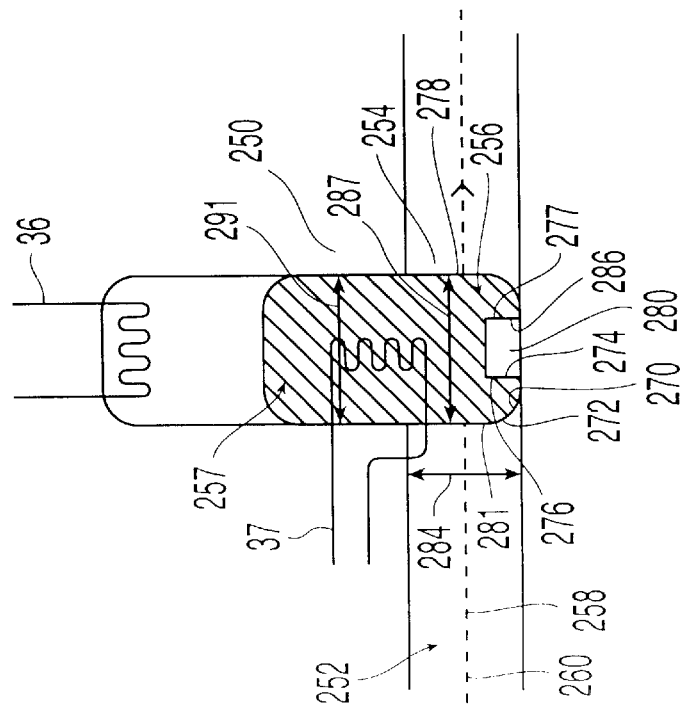
FIG. 7a shows a closed state of another valve of the invention.

Referring to FIG. 7a, a valve 250 includes a projection 280 having first and second opposed wall portions 274, 286 that cooperate to prevent leakage in response to both upstream and downstream pressure. In the closed state, a mass of temperature responsive material 256 obstructs a valve passage 268, thereby at least substantially preventing the transport of material in either direction between a first channel 252 and a second channel 254. Projection 280 is preferably centered relative to a dimension 287 of TRS 256 that is substantially aligned with a material transport path 258. Although projection 280 is shown as being substantially square, a projection having any shape, such as rectangular, triangular, or arcuate can be used.

A first abutting portion 276 of TRS 256 abuts first opposed wall portion 274 and a second abutting portion 277 of TRS 256 abuts second opposed wall portion 286. First and second abutting portions 276, and respective opposed wall portions 274, 286 substantially prevent passage of material through valve 50 when excess pressure is applied to either a first side 276 or a second side 278 of TRS 256. For example, excess upstream pressure acting upon second side 278 urges second abutting portion 277 against opposed wall portion 286, thereby closing valve 250 more securely. Valve 250 responds similarly when excess upstream pressure acts upon first side 281. Thus, valve 250 operates as a two-way valve to prevent leakage in response to excess pressure from either of two flow directions. To more securely close valve 250, at least a third abutting portion 274 abuts a valve wall 270, which is preferably substantially aligned with a central axis 260 of first channel 252.

In one embodiment of the present invention, a length of the thermally responsive substance that is aligned with a material transport path is greater than at least one of a width of the passage obstructed by the thermally responsive substance and a width of an upstream channel. As used herein, the term length refers to a distance along a material transport path, which is preferably aligned with a central axis of a channel or passage. The term width refers to the larger dimension of a channel or passage that is opposed to a material transport path or central axis therethrough. Referring to FIG. 7a, for example, a dimension or length 287 of TRS 256 is greater than a width 289 of passage 268 and a width 284 of first channel 252. A dimension or width 291 of reservoir 255 is preferably at least as large as length 287. Dimension 287 of TRS 256 is at least 15%, preferably at least 25%, and more preferably at least 30% greater than width 284 of first channel 252.

Referring to FIG. 7b, an open state of valve 250 is shown in which TRS 256 has been essentially fully retracted into reservoir 255 to open passage 268, thereby permitting passage of material through valve 250. Because TRS 256 is essentially fully retracted into reservoir 255 rather than being dispersed in a downstream direction or left in passage 268, abutting portions 276, 277 can still exhibit an impression of projection 280.

A minimum opening distance 292 from TRS 256 to outer wall 288 of projection 280 is sufficiently large to allow material to be passed through the passage at a desired material transport rate. Although FIG. 7b shows valve 250 in a fully open state, it should be understood that valve 250 can be operated in a partially open state, in which third abutting portion 272 is intermediately disposed between a fully closed position abutting wall 270 and a fully opened position substantially aligned with a first channel wall 273. As discussed above, an open state of valve 250 can be repeatedly repositioned between the opened and closed states without a significant loss of material 256 or capacity to prevent transport of material when closed.

Figure 8B:
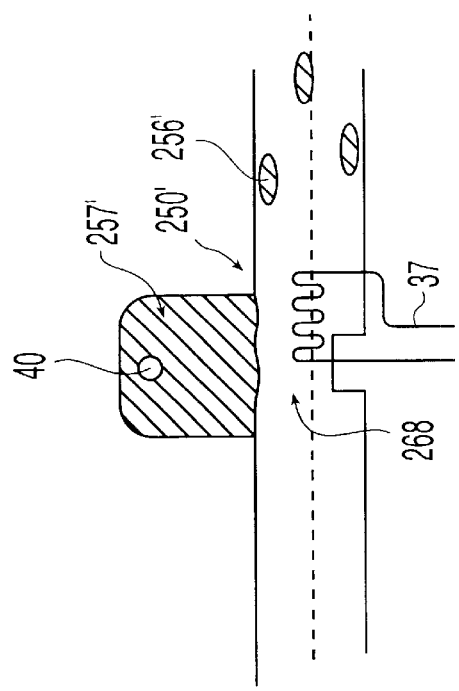
Figure 8A:
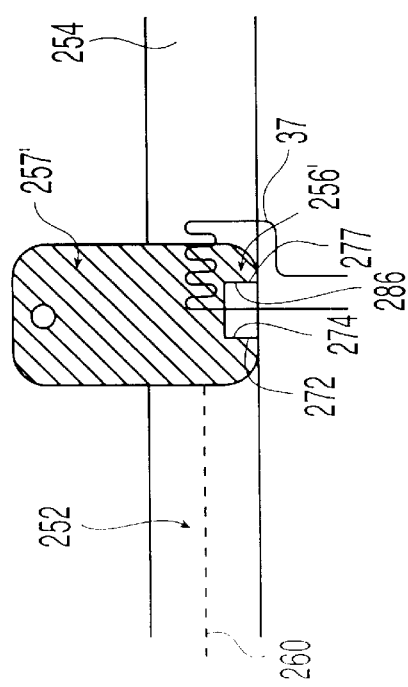
FIG. 8a shows a closed state of another valve of the invention.

A gate valve 250', seen in FIGS. 8a and 8b operates to close the valve similarly to valve 250. In opening a passage 268', valve 250' operates similarly to valve 50' in that a mass of TRS 256' obstructing passage 268' disperses or melts and enters a downstream channel, thereby opening the valve. The dispersal or melting preferably occurs upon actuation of a heat source 37 in thermal contact with TRS 256.

Figure 9B:
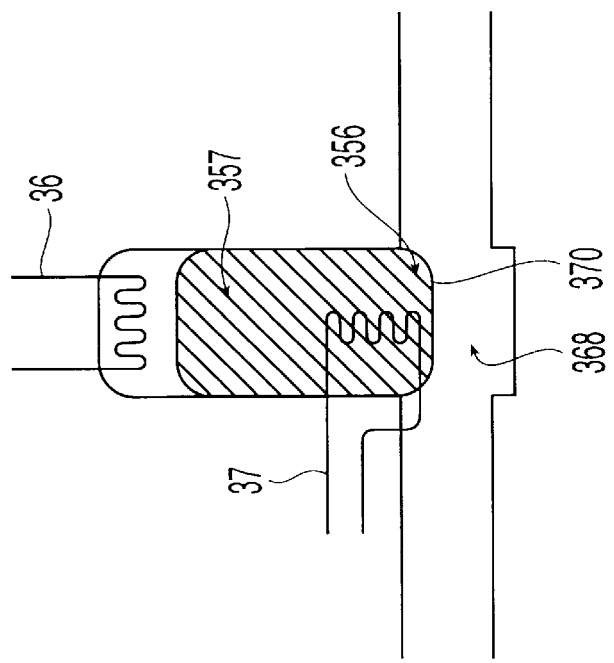
Figure 9A:
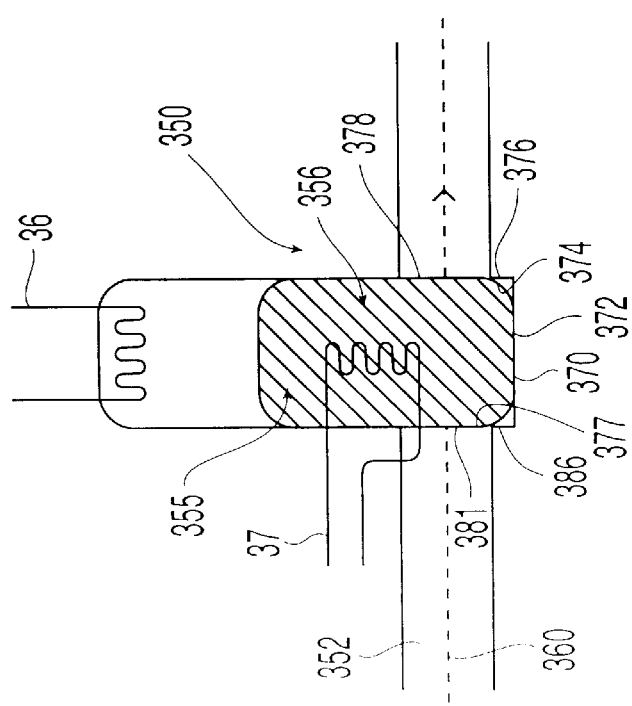
FIG. 9a shows a closed state of another valve of the invention.

Referring to FIG. 9a, a valve 350 includes an opposed wall portion 374 that does not extend into a material transport path 360 of a first channel 352. In the closed state, a mass of thermally responsive substance 356 obstructs a passage 368. A first abutting portion 376 of TRS 356 abuts first opposed wall portion 374. Excess upstream pressure present at a first surface 376 of TRS 356 urges first abutting portion 376 against first opposed wall portion 374, thereby closing valve 350 more securely.

Valve 350 preferably includes a second opposed wall portion 386 that also does not extend into material transport path 360. First and second opposed wall portions 374, 386 oppose one another so that valve 350 operates as a two-way valve. Thus, excess upstream pressure present at a second surface 378 of TRS 356 urges a second abutting portion 377 of TRS 356 against second opposed wall portion 386.

In the open state, FIG. 9b, valve 350 TRS 356 is retracted into reservoir 355, thereby opening passage 368 to the passage of material.

Figure 10B:
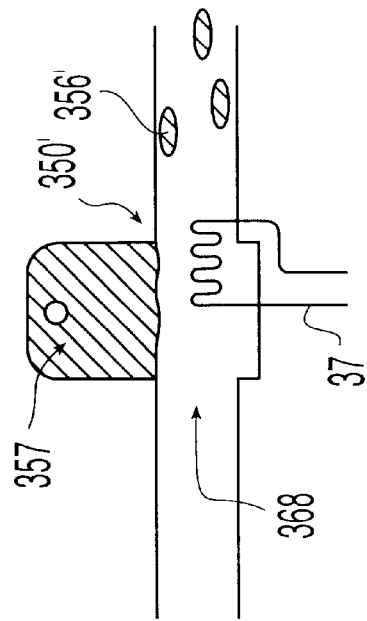
Figure 10A:
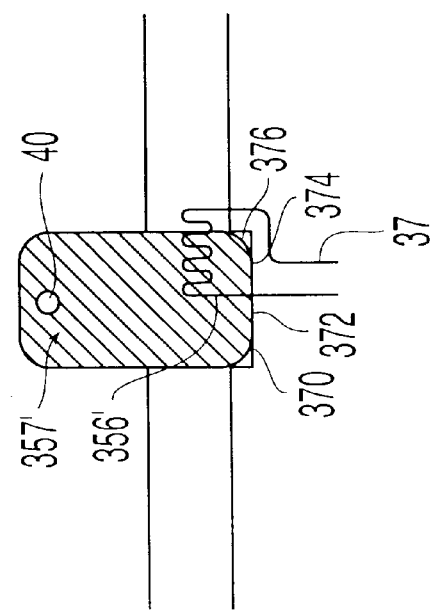
FIG. 10a shows a closed state of another valve of the invention.

A gate valve 350', seen in FIGS. 10a and 10b operates close similarly to valve 350. In opening a passage 368', valve 350' operates similarly to valve 50' in that a mass of TRS 356' obstructing passage 368 disperses or melts, thereby opening the valve. The dispersal or melting preferably occurs upon actuation of a heat source 37 in thermal contact with TRS 356'. Preferably, substantially all of TRS 356' enters second channel 354, downstream from valve 350'.

Referring to FIGS. 11a–11d an embodiment of a valve 450 having a surface 500 configured to provide capillary assisted loading is shown. Valve 450 defines a passage 468 between first and second channels 452, 454. A temperature responsive substance, which, for clarity, is not shown in FIGS. 11a–11c, operates to open and close the valve, as discussed above. In one embodiment, for example, the opening of valve 450 comprises a retraction motion of TRS 456 into a reservoir 455. In the preferred embodiment, the opening of passage 468 comprises a dispersing or melting of TRS 456, which enters at least one downstream channel, thereby opening passage 468.

Loading surface 500 is configured to limit the amount of TRS that enters channels 452, 454 when TRS 456 is introduced into passage 468. An opening 515 between passage 468 and first channel 452 defines a cross sectional area 516, which is at least 40% smaller, preferably at least about 50% smaller, than an adjacent cross sectional area 518 within first channel 452. Similarly, an opening 520 between passage 468 and second channel 454 preferably has a smaller cross sectional area than an adjacent cross sectional area within second channel 454.

The reduced cross section of the passage openings is preferably achieved by reducing a height of the passage. As used herein, a height of a channel or passage refers to the smallest dimension of the channel or passage. For example, a distance 502 between loading surface 500 and an opposed surface 504 is less than corresponding distances 506 and 507 between opposed surfaces of first and second channels 452 and 454, respectively. Distance 502 is at least about 40% preferably at least about 50%, and more preferably at least about 65% less than distances 506, 507.

Figure 11D:
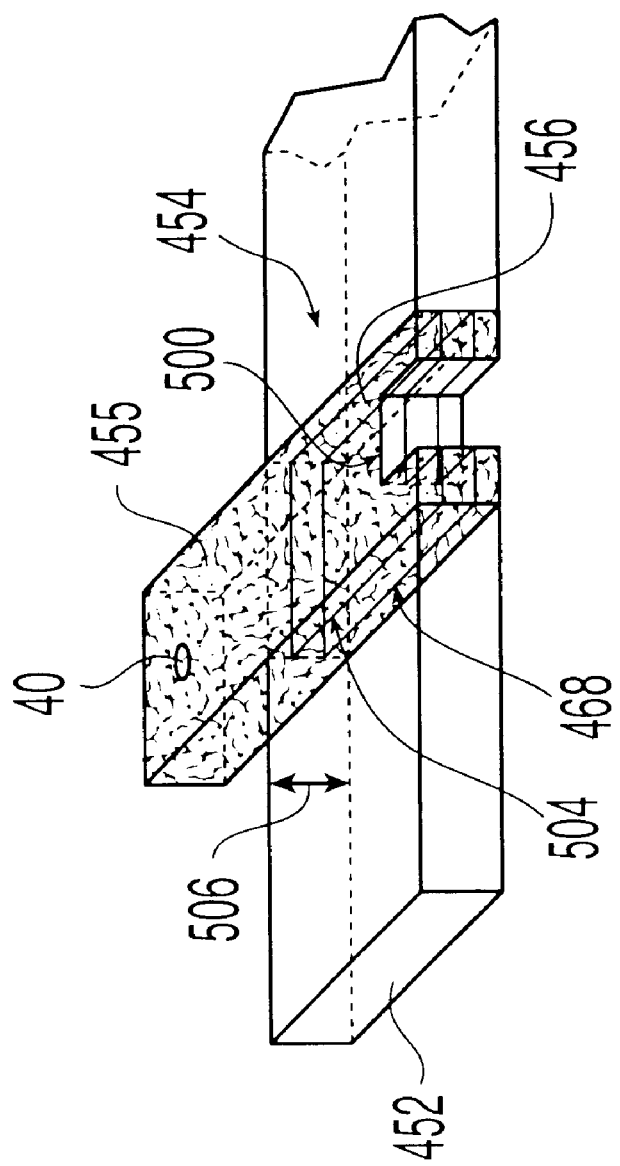

To load TRS into passage 468, a reservoir 455 and passage 468 are heated sufficiently to allow motion of the TRS therein. TRS is introduced through access port 40. Capillary action draws TRS into passage 468. Upon encountering first and second openings 510 and 512, however, TRS in passage 468 encounters resistance, such as that caused by the surface tension of the TRS resisting the expansion of the surface area upon moving from the lower cross-sectional area opening into first and second channels 452, 454. Thus, as seen in FIG. 11*d*, loading surface 500 allows the introduction of an amount of TRS that is sufficient to obstruct the passage of a valve but insufficient to enter adjacent channels 452 and 454.

Valve 450 can include at least one opposed surface, such as opposed wall portion as described above, to prevent leakage in response to excess pressure present in either of channels when the valve is closed.

Figure 12B:
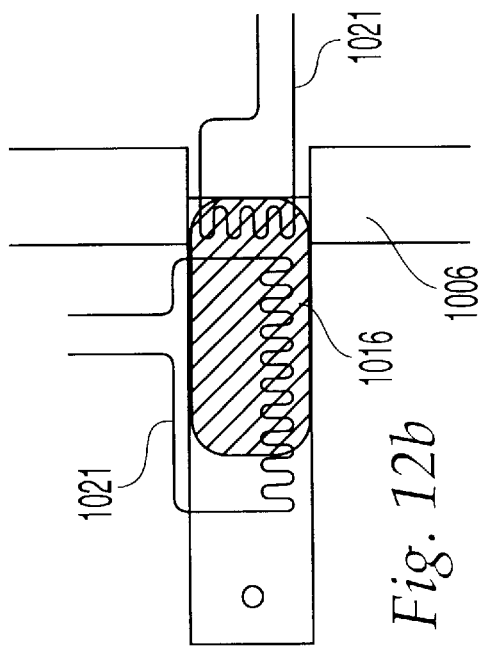
FIGS. 12a–12c show top views of a capillary assisted loading valve of the invention.
Figure 12C:
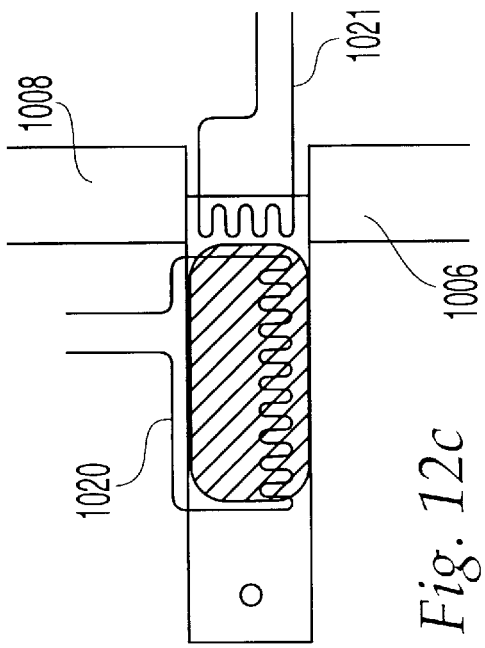
Figure 12A:
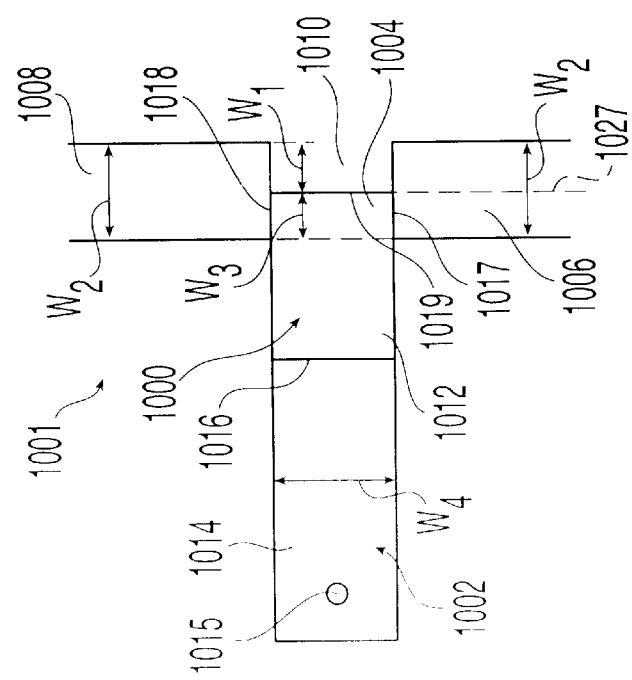
Figure 13A:
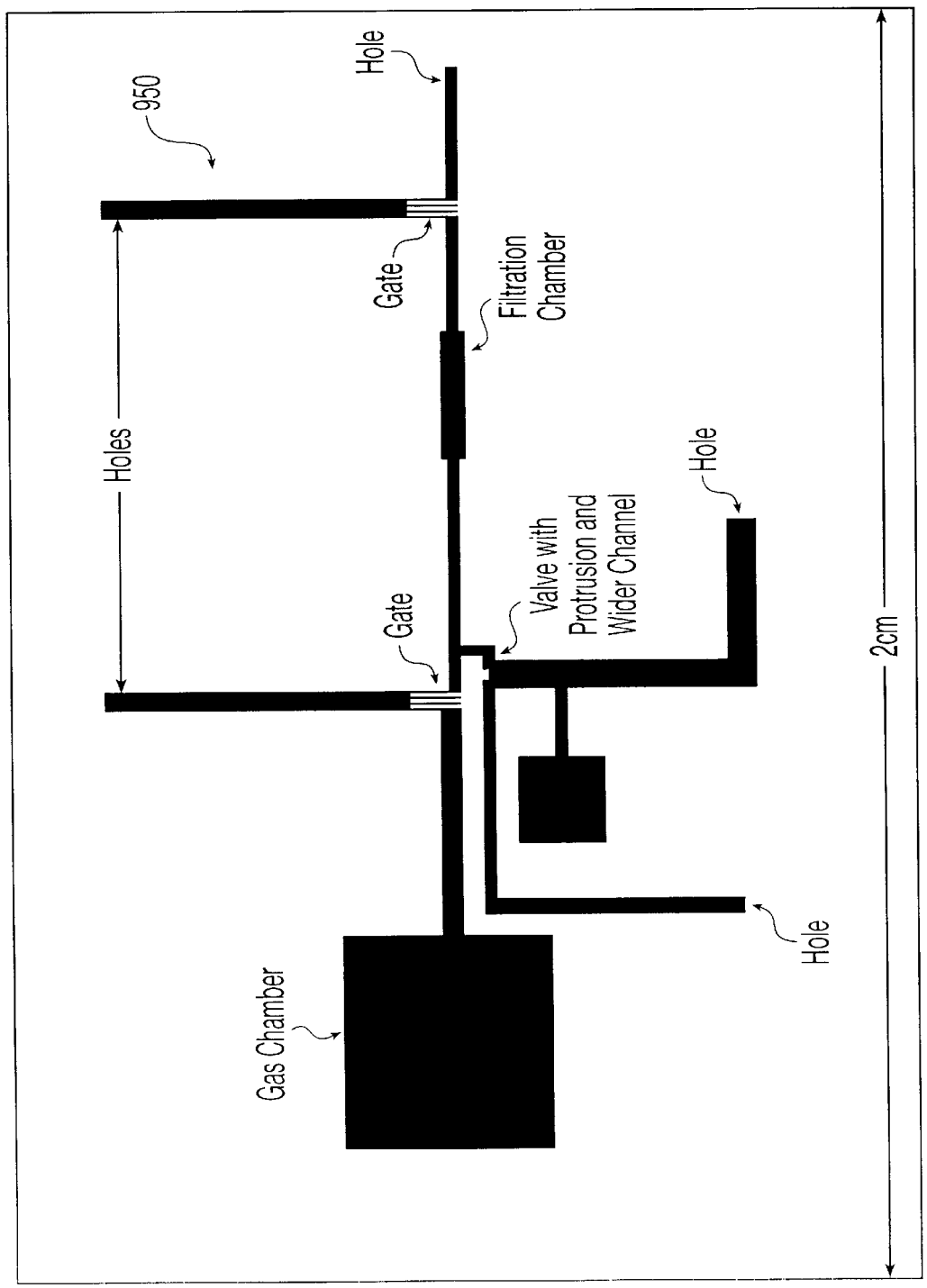
Figure 13B:
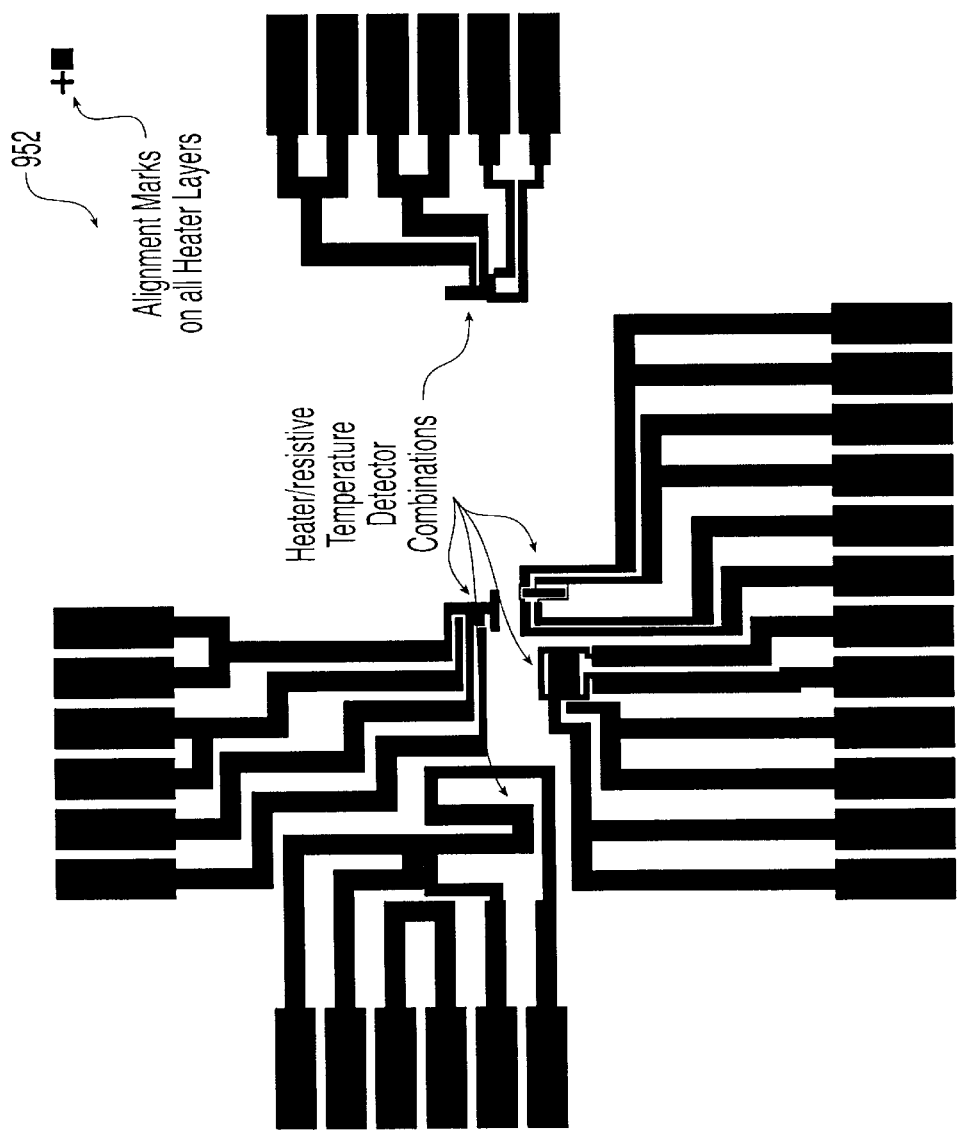
Figure 13D:
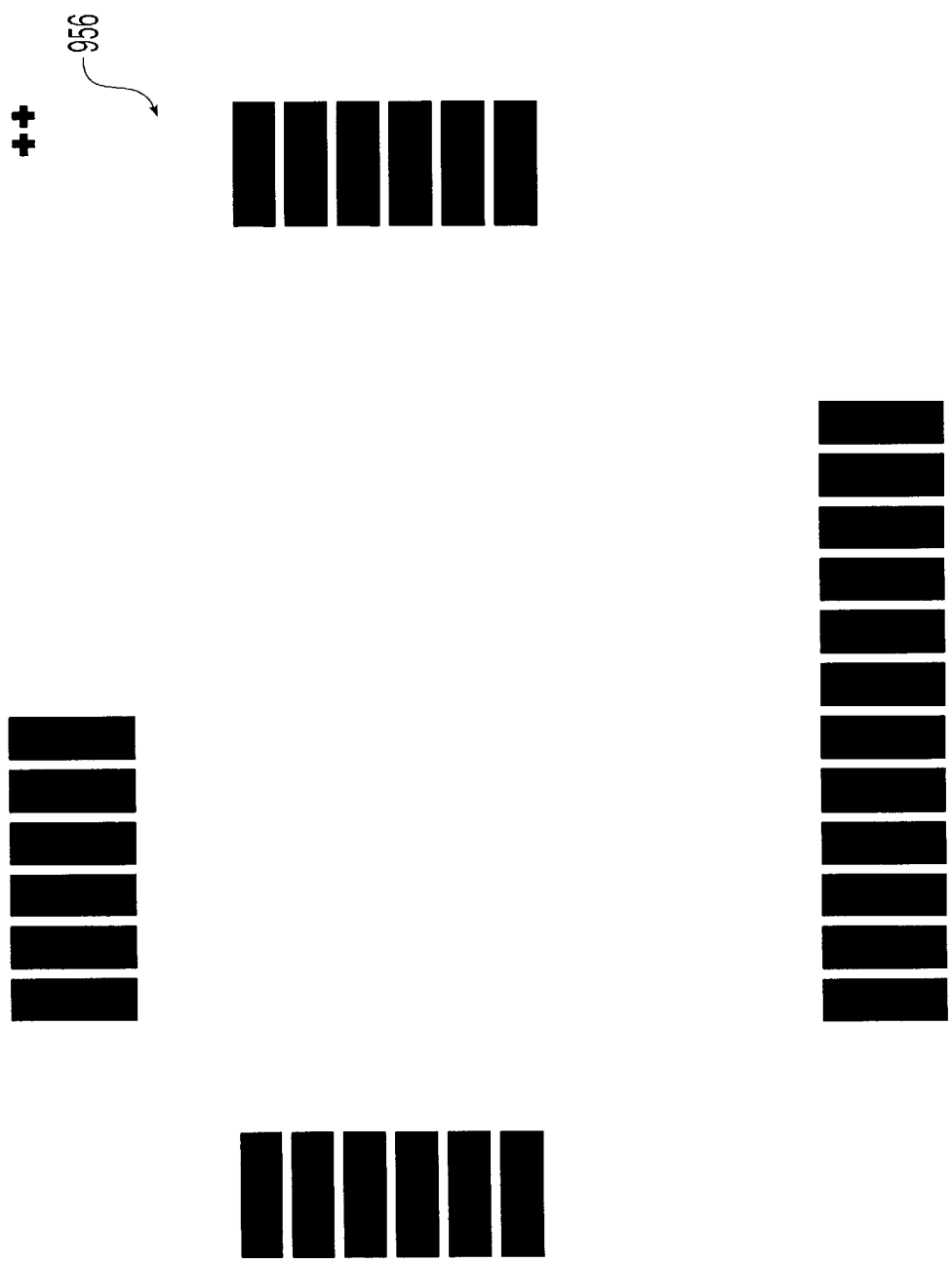

Referring to FIGS. 12*a*–12*c*, a valve 1001 has a loading surface 1000 that extends from a passage 1004 into a reservoir 1002. For clarity, heat sources and TRS associated with valve 1001 are not shown in FIG. 12*a*. Valve 1001 includes first and second channels 1006, 1008 and a protrusion 1010. Protrusion 1010 extends for a width $w_1$ into passage 1004 so that a width $w_3$ of the passage is less than a width $w_2$ of first and second channels 1006, 1008. Width $w_3$ is preferably from about 25% to about 75%, such as about 50% of width $w_2$. Width $w_3$ is preferably from about 25% to about 75%, such as about 50%, of a width $w_4$ of reservoir channel. The widths of first and second channels 1006, 1008 are preferably, but not necessarily, the same. However, if one of the first or second channels is made wider, its height would have to be correspondingly reduced. The width $w_4$ of the reservoir can be wider or narrower than the width $w_2$ of the first and second channels.

Loading surface 1000 reduces a height of passage 1004 and of a loading portion 1012 of reservoir channel 1002. Preferably, the height of passage 1004 and loading portion 1012 is from about 25% to about 75%, such as about 50% of a height of first and second channels 1006, 1008 and of a height of a distal portion 1014 of reservoir 1002.

To load valve 1001, an amount of TRS is introduced through a hole 1015 until a leading edge of the TRS reaches edge 1016 of loading surface 1000. Heat sources 1020 and 1021 are used to raise the temperature of reservoir 1002 and passage 1004 to a temperature sufficient to allow the TRS to flow. Upon reaching edge 1016, capillary action draws the TRS into loading portion 1012 and passage 1004. Upon reaching first and second edges 1017 and 1018, surface tension substantially prevents the TRS from entering first and second channels 1006, 1008. When a portion of the TRS contacts surface 1019 of protrusion 1010, as shown in FIG. 12*b*, the valve is in the closed state to substantially prevent the passage of material between first and second channels 1006, 1008.

To open valve 1001, the temperature of the TRS obstructing passage 1004 is raised to a temperature sufficient to allow at least a portion of the TRS obstructing the passage 1004 to disperse or melt and enter at least one of first and second channels 1006, 1008. Pressure, such as air or liquid pressure, from one of the first and second channels preferably displaces the TRS obstructing the channel once the temperature has been raised. During the opening operation, the temperature of the TRS in the reservoir is preferably not raised by an amount sufficient to disperse or melt the TRS. Valve 1001 can be returned to the closed state by heating TRS present in reservoir 1002. Capillary action will draw the TRS into passage 1004, as discussed above.

Valve 1001 can be opened and closed repeatedly as long as an amount of TRS remains in the distal portion of reservoir 1002. The amount of TRS present in the distal portion of the reservoir is preferably greater than the amount of TRS that was dispersed upon opening the passage. Preferably, the dispersed TRS enters one of the first or second channels. The amount of TRS in the distal portion of the reservoir is preferably at least slightly greater than the amount of TRS in the loading portion to ensure that the TRS will fully re-close passage 1004.

The mean radius of curvature (MRC) of a distal end of TRS within the distal portion 1014 of reservoir 1002 is preferably greater than the MRC of a proximal end of TRS within the loading portion 1000 or within the passage 1004. By distal, it is meant that portion of the TRS that is spaced apart from passage 1004, by proximal it is meant that portion of the TRS that is adjacent or within passage 1004. Preferably, the contact angle of the TRS with walls of the loading portion is substantially constant.

Valve 1001 can also include an opposing surface, such as that shown in FIGS. 11*a*–11*d*, to assist in preventing the passage of material when the valve is in the closed state. Valve 1001 can also be configured as a non-capillary assisted loading valve in which loading surface 1000 is absent.

A constant channel width is not required. Thus, channels of varying width may be used. The tendency of a TRS to move in a given direction is governed by the ratio between the mean radius of curvature of the front of the drop and the mean radius of curvature of the back of the drop. These curvatures are based on the contact angle of the fluid with the material and the dimensions of the channel.

Returning to FIG. 1, the structure and operation of microfluidic system 700 is discussed in further detail. Chamber 704, defined in substrate 701, is preferably configured to perform at least one chemical or physical process using material therein. Material includes samples and reagents such as, for example, fluids, particles, such as cells, DNA, viruses, and particle containing fluids. In one embodiment, chamber 704 can be configured to mix a sample with a reagent to facilitate a chemical reaction. Alternatively, chamber 704 can be configured to concentrate or dilute a sample. Other processes, such as PCR amplification, filtering, and the like are also possible. It should be understood that chamber 704 can have the same dimensions as a channel.

An outlet channel 710 is provided as an outlet to remove excess sample or reagent materials from chamber 704. During operation of chamber 704, a valve 712, is operated in the open state to allow material to exit chamber 704 via channel 710. Preferably, channel 710 includes a flow through member, such as a filter, to allow only selected material to exit chamber 704 via channel 710. A valve 714 prevents material within chamber 704 from entering a downstream channel 716. A valve 718 prevents material within chamber 704 from entering an on-board pressure source 720, which is preferably a thermally actuated type, as discussed above. Pressure source 720 preferably provides a sufficient gas pressure and gas volume to drive material present in chamber 704 into downstream channel 716.

Upon completion of any process carried out within chamber 704, valve 712 is closed to prevent any material from exiting chamber 704 via channel 704. To allow material to enter downstream channel 716, pressure source 720 and heat sources associated with valves 714 and 718 are actuated thereby opening both valves. Material is transported through a passage of valve 714 into downstream channel 716 for analysis or further processing. Downstream processing chambers preferably include chambers to lyse cells, such as bacterial cells. Example bacteria include Group B streptococcus and bacteria associated with bacterial menengitis. Cells can be lysed to release nucleic acids therein, as known in the art by contacting the cells with a lysing agent, such as a surfactant and/or buffer. Thus, the system is preferably provided with a reservoir of buffer connected by a channel to the lysing chamber. A second downstream processing chamber is preferably configured to perform a PCR reaction upon nucleic acids released from the lysed cells. The PCR chamber is joined by channels configured to introduce reagents, such as enzymes and buffers suitable to facilitate the amplification of the nucleic acids.

The opening and closing of the valves herein preferably operate automatically under computer control. System 700 preferably includes contacts 720, which provide electrical or optical communication with various on-board system elements, such as valves, heaters, procession chambers, sensors to detect the state of valves, and the like. Preferred computer control systems and methods for operating thermally actuated valves are disclosed in U.S. patent application Ser. No. 09/819,105 filed Mar. 28, 2001, which is hereby incorporated herein in its entirety.

Substrate defining elements such as channels and valves can be formed of any suitable material, such as silicon, quartz, glass, and polymeric materials. The substrate can be homogenous or formed of one or more elements bonded together, such as a silicon substrate having a bonded quartz cover. The cover and substrate are micromachined with system features, including the valves, passages, channels, heaters. Micromachining includes fabrication techniques, such as photolithography followed by chemical etching, laser ablation, direct imprinting, stereo lithography, and injection molding. For example, a preferred microfluidic system is fabricated by injection molding of a substrate comprising one or more cyclic olefins.

Referring to the inset of FIG. 1, a valve 714 includes upstream and downstream channels 1030, 1031 and a reservoir 1032. For clarity, TRS associated with valve 714 is not shown. Valve 714 includes a protrusion 1034 and an opposing surface 1033 associated with a passage 1035.

Referring to FIGS. 13a–13d, photolithographic masks suitable for using in micromachining a system of the invention are shown. Photolithography provides one approach for fabricating a microfluidic system. An example photolithographic process begins by deposit a metal, such as at least one of chrome and gold, onto a substrate. Techniques such as vapor deposition or electron beam sputtering can be used to deposit the metal layer. A preferred substrate for fabricating channel, passage, and valve elements is a 500 micron thick Dow Coming 7740 Pyrex wafer. The wafer is coated with a layer of photo-resist, such as by spin coating. A photolithographic mask 950 indicative of the elements to be microfabricated is used as a pattern. The substrate is exposed to a light source with the mask in place and the resist is developed. Patterning removes the resist from areas of the substrate that will be etched.

An etchant, such as an acid, is used to remove the metal layer protecting regions of the substrate where the resist had been removed. The resulting unprotected areas of the substrate are etched, preferably to a depth of about 50 microns, using an etchant, such as buffered hydrofluoric acid. Once etching is complete, the remaining resist and metal is removed. Holes are drilled to allow the introduction of thermally responsive material, as described above.

Heater elements are preferably fabricated upon a second substrate, such as a 500 micron thick quartz wafer. A metal, such as a 2500 angstrom thick layer of aluminum, is deposited onto the substrate, which is then coated with a layer of resist. The coated substrate is masked using a mask 952 and patterned as described above. Aluminum is removed, such as by etching, from the areas of the substrate where the resist has been removed. Subsequently, the remaining resist is stripped away.

A low temperature oxide layer is deposited onto the substrate. A layer of metal, such as a chrome-gold layer, is deposited over the oxide layer. The metal layer is coated with resist and patterned with a third mask 954, which preferably defines the pattern that will become the recess, which receives a flow through member. The chrome gold layer is etched to form the recess.

The low temperature oxide is etched to a depth of about 100 microns using and etchant such as an aqueous hydrofluoric/nitric acid mixture. The resist and chrome gold layer is removed. Subsequently, a the oxide layer is coated with a layer of resist and patterned with a fourth mask 956, which preferably defines the pattern for electrical contacts to the system. An etchant, such as buffered hydrofluoric acid is used to etch through the exposed oxide. Holes are drilled through the second substrate directly opposite to where the channel will be. The first and second substrate are bonded together, as understood in the art.

Stereolithographic approaches for fabricating systems of the invention increase the efficiency of prototyping and in manufacturing microfluidic devices. Hi-resolution (about 0.004" spot size) stereolithography allows channel designs to be rapidly formed into a working system. The time savings, cost savings, and flexibility of the stereolithography allows us to test more designs more quickly and cheaply than ever before.

The epoxy-based resins used by the conventional stereolithography devices are not well suited to some uses in microfluidic devices. They cannot withstand high temperatures, they absorb fluids (slowly), they are fluorescent under an excitation source, and they are not optically clear. These properties are not obstacles to basic fluidic tests, but for full tests of device functionality and for manufacture, a material with more robust properties and a method for forming it is needed. A material line from Ticona (a subsidiary of Celanese A. G.) called Topas, such as Topas 5013 can be used. The Topas material is formed by an injection molding process. The mold halves for this process are generated by stereolithography. This reduces the lead-time usually necessary to create molds. For short run parts, this method works well. In the long run, steel molds are preferably created. Injection molded parts represent a dramatic cost savings over parts that are created in glass and quartz by a photolithographic process.

While the above invention has been described with reference to certain preferred embodiments, it should be kept in mind that the scope of the present invention is not limited to these. Thus, one skilled in the art may find variations of these preferred embodiments which, nevertheless, fall within the spirit of the present invention, whose scope is defined by the claims set forth below.

What is claimed is:

1. A valve for use in a microfluidic system, comprising:
   a substrate defining an upstream channel and a downstream channel joined by a passage, the passage comprising a first surface; and
   a thermally responsive substance (TRS) disposed, when the valve is in the closed state, to substantially obstruct the passage, wherein pressure present in the upstream channel urges at least a portion of the TRS against the first surface; and
   a reservoir adjacent the passage, wherein, upon an opening motion of the TRS, at least at least a portion of the TRS moves into the reservoir thereby opening the passage.

2. The valve of claim 1, wherein the passage defines a central axis and the first surface is disposed at an angle to the central axis.

3. The valve of claim 1, further comprising a microfabricated heat source in thermal contact with the TRS.

4. The valve of claim 1, wherein the substrate is a planar substrate and the upstream channel, downstream channel, and passage are etched in a surface of the substrate.

5. The valve of claim 1, wherein the passage further comprises a second surface disposed at a second angle to the central axis, and wherein at least a second portion of the TRS that obstructs the passage abuts the second surface.

6. The valve of claim 5, wherein the first and second surfaces protrude into the passage.

7. The valve of claim 5, wherein the first and second surfaces form a restriction therebetween.

8. The valve of claim 1, wherein the substrate comprises silicon.

9. The valve of claim 3, further comprising a second, different substrate and wherein the microfabricated heat source is microfabricated on a surface of the second, different substrate.

10. The microfluidic system of claim 3, wherein the heat source comprises a heating element disposed at a second surface of the second substrate, the second surface of the second substrate being opposite the first surface of the second substrate.

11. A method for producing a valve for a microfluidic system, comprising:
   providing a first substrate having a first planar surface and a second, different substrate having a first planar surface, a portion of the first planar surface of the first substrate bonded with a portion of the first planar surface of the second substrate, whereby the first and second substrates define, therebetween, a passage that joins an upstream channel and a downstream channel of the microfluidic system, the passage comprising a retaining surface; and
   introducing a mass of temperature responsive material (TRS) into the passage, wherein introducing the mass of TRS comprises heating the passage to allow motion of the TRS therein, and wherein, when the valve is in the closed state, pressure in the upstream channel urges the TRS against the retaining surface.

12. A method for producing a valve for a microfluidic system, the valve being produced in the closed state, comprising:
   providing a substrate defining a passage that joins an upstream and a downstream channel of the microfluidic system; and
   introducing a mass of temperature responsive material (TRS) into a reservoir channel adjacent the passage, wherein capillary action draws the TRS into the passage, and wherein, upon being drawn into the passage, the TRS obstructs the passage and a surface tension of the TRS substantially prevents the TRS in the passage from entering the upstream or downstream channel.

13. A microfluidic system comprising a valve for providing a passage between an upstream and a downstream channel of the microfluidic system, the [valve] microfluidic system comprising:
   a first substrate having a first planar surface and a second, different substrate having a first planar surface, a portion of the first planar surface of the first substrate bonded to a portion of the first planar surface of the second substrate, whereby the first and second substrates define, therebetween, at least an upstream channel and a downstream channel joined by a passage; and
   a temperature responsive substance (TRS), wherein, at a first temperature, the TRS is disposed to obstruct the passage, and wherein, at a second temperature, at least a portion of the (TRS) enters the downstream channel, thereby opening the passage.

14. The valve of claim 13, wherein at least about 75% of the TRS that obstructs the passage enters the downstream channel upon the opening of the passage.

15. A microfluidic system comprising a valve for providing a passage between upstream and downstream channels of the microfluidic system, comprising:
   a first substrate having a first planar surface and a second, different substrate having a first planar surface, a portion of the first planar surface of the first substrate bonded to a portion of the first planar surface of the second substrate, whereby the first and second substrates define, therebetween, at least an upstream channel and a downstream channel joined by a passage;
   a temperature responsive substance (TRS) configured to substantially obstruct the passage;
   a heat source disposed in thermal contact with the (TRS), wherein, upon actuation of the heat source, at least a portion of the (TRS) enters the downstream channel, thereby opening the passage.

16. The valve of claim 15, wherein the passage comprises a first surface, wherein pressure present in the upstream channel urges at least a portion of the TRS against the first surface.

17. The valve of claim 16, wherein the passage further comprises a second surface, wherein pressure present in the upstream channel urges at least a portion of the TRS against the second surface.

18. The valve of claim 17, wherein the first and second opposed walls define a restriction therebetween.

19. The valve of claim 15, wherein the heat source is configured to heat at least a portion of the downstream channel to substantially prevent (TRS) that enters the downstream channel from obstructing the channel.

20. The microfluidic system of claim 15, wherein the heat source comprising a heating element is disposed at a second surface of the first substrate, the second surface of the first substrate being opposite the first surface of the first substrate.

21. A microfluidic system, comprising:
   a first substrate having a first planar surface and a second substrate having a first planar surface, the first planar surface of the first substrate bonded with the first planar surface of the second substrate, whereby the first and second substrates define, therebetween, a processing chamber, a source channel, and a downstream channel, the source channel joining the processing chamber at a first point and the downstream channel joining the processing chamber at a second point;
   a thermally responsive substance (TRS) disposed to obstruct a passage between the processing chamber and downstream channel; and
   a heat source in thermal contact with the TRS, wherein, upon actuation of the heat source, at least a portion of the TRS enters the downstream channel, thereby opening the passage.

22. A valve for use in a microfluidic system, comprising:
   a thermally responsive substance (TRS) disposed to substantially obstruct the passage, wherein a length of the TRS obstructing the passage is greater than a width of the upstream channel adjacent the passage; and
   a heat source in thermal contact with the TRS, wherein, upon actuation of the heat source, at least a portion of the TRS obstructing the passage moves out of the passage, thereby opening the passage.

23. The valve of claim 22, further comprising a reservoir of TRS adjacent the passage, wherein a width of the reservoir is greater than the width of the upstream channel.

24. The valve of claim 23, wherein the opening motion comprises a retraction of the TRS into the reservoir.

25. The valve of claim 22, wherein the passage comprises a surface and pressure present in the upstream channel urges at least a portion of the TRS against the surface.

26. The valve of claim 22, wherein at least 50% of the TRS moves out of the passage thereby opening the passage.

27. A valve for use in a microfluidic system, comprising:
   a substrate defining a first and second channel joined by a passage, the first channel and the passage defining an opening therebetween;
   a thermally responsive substance (TRS) disposed to substantially obstruct the passage, wherein a height of the opening is less than a height of the first channel adjacent the opening such that capillary action draws TRS into the passage and a surface tension of the TRS substantially prevents the TRS from entering the first or second channel; and
   a heat source in thermal contact with the TRS, wherein, upon actuation of the heat source, an opening motion of the TRS opens the passage.

28. The valve of claim 27, wherein the second channel and the passage define an second opening therebetween, and further wherein a height of the second opening is less than a height of the second channel adjacent the passage.

29. The valve of claim 28, wherein the heights of each of the first and second openings are at least about 50% less than the corresponding heights of the first and second channels, respectively.

30. The valve of claim 27, further comprising:
   a reservoir adjacent the passage, a height of the reservoir at a first location being less than a height of the reservoir at a second location, the first location being closer to the passage than the second location.

31. The valve of claim 30, wherein the reservoir comprises an a port for introducing TRS to the reservoir.

32. A microfluidic system, comprising:
   a first planar substrate and a second, different planar substrate, a first surface of the first substrate and a first surface of the second substrate defining, therebetween, at least an upstream channel and a downstream channel joined by a passage, the passage comprising a first surface; and
   a thermally responsive substance (TRS), at least a first portion of the TRS disposed, when the passage is in the closed state, to substantially obstruct the passage, wherein pressure present in the upstream channel urges at least a portion of the first portion of the TRS against the first surface of the passage.

33. A method for producing a valve for a microfluidic system, the valve being produced in the closed state, comprising:
   providing a substrate defining a passage that joins an upstream and a downstream channel of the microfluidic system; and
   introducing a mass of temperature responsive material (TRS) into a reservoir channel adjacent the passage;
   heating at least the reservoir channel and passage, wherein capillary action draws at least a portion of the TRS into the passage thereby obstructing the passage.

34. A method for producing a valve for a microfluidic system, the valve being produced in the closed state, comprising:
   providing a substrate defining (1) a passage that joins an upstream and a downstream channel of the microfluidic system and (2) a reservoir joining the passage, wherein a height of the reservoir at a first location is less than a height of the reservoir at a second location, the first location of the reservoir being closer to the passage than the second location;
   heating at least the reservoir and passage;
   introducing a mass of temperature responsive material (TRS) into the reservoir at least until a portion of the TRS reaches the first location of the reservoir, wherein capillary action draws TRS into the passage thereby obstructing the passage.

* * * * *